(12) United States Patent
Takeda et al.

(10) Patent No.: US 7,752,594 B2
(45) Date of Patent: Jul. 6, 2010

(54) SEMICONDUCTOR FAILURE ANALYSIS APPARATUS, FAILURE ANALYSIS METHOD, FAILURE ANALYSIS PROGRAM, AND FAILURE ANALYSIS SYSTEM

(75) Inventors: Masahiro Takeda, Hamamatsu (JP); Kazuhiro Hotta, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 549 days.

(21) Appl. No.: 11/409,273

(22) Filed: Apr. 24, 2006

(65) Prior Publication Data

US 2007/0011519 A1    Jan. 11, 2007

(30) Foreign Application Priority Data

Jun. 22, 2005    (JP)    ............................ P2005-182629

(51) Int. Cl.
*G06F 17/50* (2006.01)
(52) U.S. Cl. ................ 716/19; 716/4; 716/20; 716/21; 430/5; 430/30
(58) Field of Classification Search ...................... 716/4, 716/19–21; 430/5, 30
See application file for complete search history.

(56) References Cited

U.S. PATENT DOCUMENTS

| | | | |
|---|---|---|---|
| 5,240,866 A * | 8/1993 | Friedman et al. ............... 702/35 |
| 5,930,382 A | 7/1999 | Irie et al. |
| 6,292,582 B1 | 9/2001 | Lin et al. |
| 6,553,546 B1 | 4/2003 | Murakami |
| 6,775,817 B2 * | 8/2004 | Ono et al. ....................... 716/21 |
| 7,079,971 B2 * | 7/2006 | Fukuda ........................ 702/117 |
| 2001/0000460 A1 * | 4/2001 | Ishihara et al. ............... 382/149 |
| 2002/0024603 A1 * | 2/2002 | Nakayama et al. ........... 348/232 |
| 2002/0060650 A1 * | 5/2002 | Wakashiro et al. ............. 345/9 |
| 2002/0144219 A1 | 10/2002 | Zachariah et al. |
| 2003/0174877 A1 * | 9/2003 | Aiger .......................... 382/145 |
| 2004/0107412 A1 | 6/2004 | Pack et al. |
| 2004/0139407 A1 | 7/2004 | Mukai et al. |
| 2004/0243891 A1 * | 12/2004 | Ohta ........................... 714/721 |

(Continued)

FOREIGN PATENT DOCUMENTS

CN    1444035    9/2003

(Continued)

*Primary Examiner*—Thuan Do
*Assistant Examiner*—Nha T Nguyen
(74) *Attorney, Agent, or Firm*—Drinker Biddle & Reath LLP

(57) ABSTRACT

A failure analysis apparatus 10 is composed of an inspection information acquirer 11 for acquiring at least a pattern image P1 of a semiconductor device, a layout information acquirer 12 for acquiring a layout image P3, a failure analyzer 13 for analyzing a failure of the semiconductor device, and an analysis screen display controller 14 for letting a display device 40 display information about the failure analysis. The analysis screen display controller 14 generates a superimposed image in which the pattern image P1 and the layout image P3 are superimposed, as an image of the semiconductor device to be displayed by the display device 40, and sets a transmittance of the layout image P3 relative to the pattern image P1 in the superimposed image. This substantializes a semiconductor failure analysis apparatus, analysis method, analysis program, and analysis system capable of securely and efficiently carrying out the analysis of the failure of the semiconductor device.

19 Claims, 14 Drawing Sheets

U.S. PATENT DOCUMENTS

| | | |
|---|---|---|
| 2005/0076316 A1* | 4/2005 | Pierrat et al. .................... 716/4 |
| 2005/0147287 A1 | 7/2005 | Sakai et al. |
| 2006/0098862 A1* | 5/2006 | Demarest et al. ............ 382/145 |
| 2006/0215901 A1 | 9/2006 | Nakagaki et al. |
| 2007/0020781 A1 | 1/2007 | Majima et al. |
| 2007/0230770 A1 | 10/2007 | Kulkarni et al. |
| 2007/0294053 A1 | 12/2007 | Majima et al. |

FOREIGN PATENT DOCUMENTS

| | | |
|---|---|---|
| JP | 04-138574 | 5/1992 |
| JP | 5-181924 | 7/1993 |
| JP | 08-250560 | 9/1996 |
| JP | 10-004128 | 1/1998 |
| JP | 10-063235 | 3/1998 |
| JP | 11-016974 | 1/1999 |
| JP | 2001-201545 | 7/2001 |
| JP | 2001-203248 | 7/2001 |
| JP | 2003-86689 | 3/2003 |
| JP | 2003-086689 | 3/2003 |
| JP | 2003-282665 | 10/2003 |
| JP | 2003-303746 | 10/2003 |
| JP | 3519872 | 2/2004 |

* cited by examiner

Fig.3
(a) 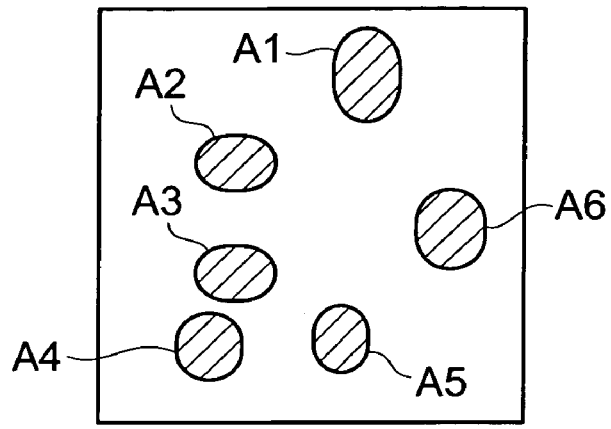
(b) 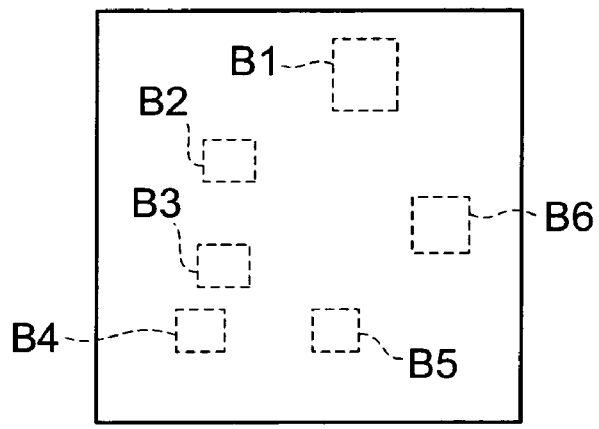
(c) 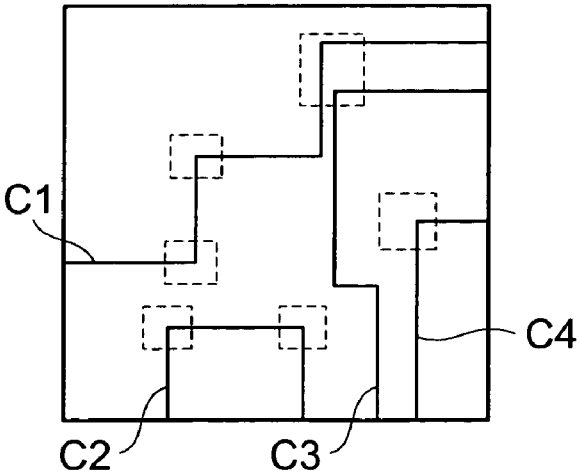

Fig.4
(a)
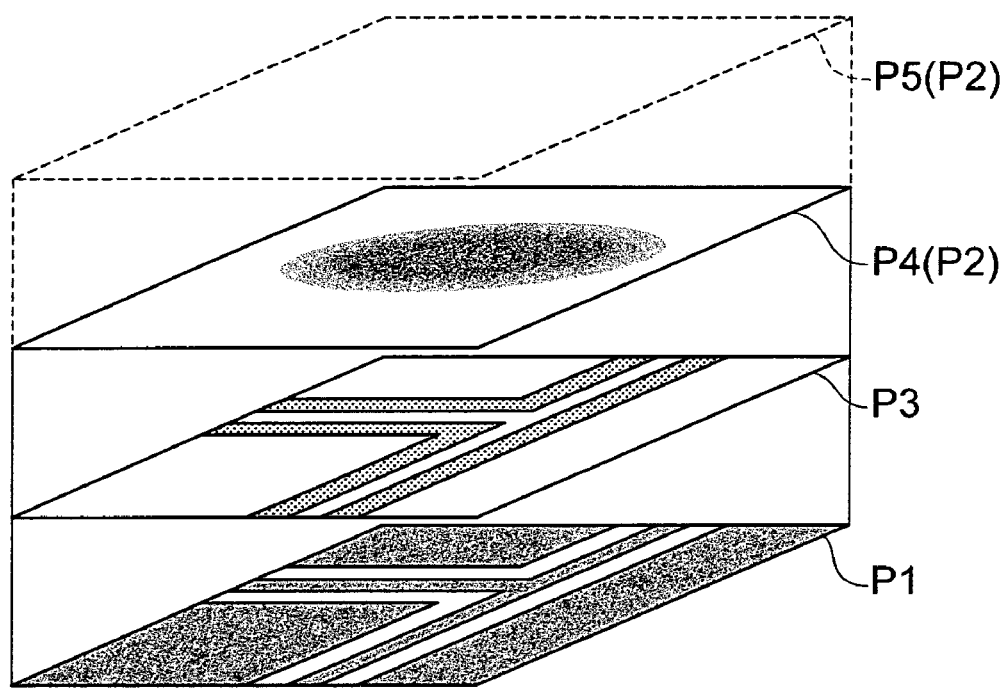
(b)
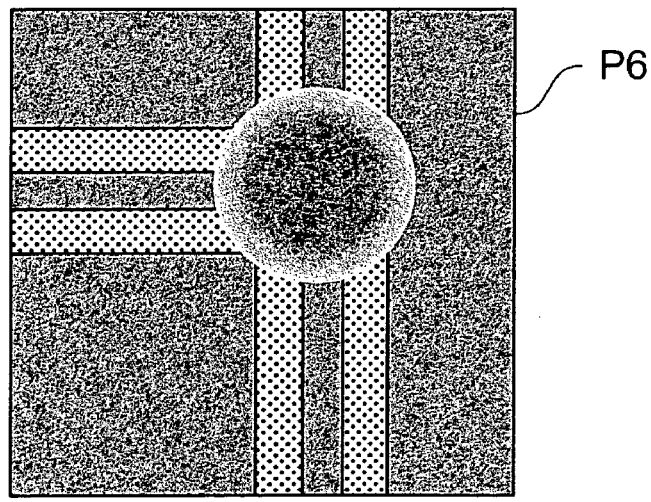

Fig.5
(a)
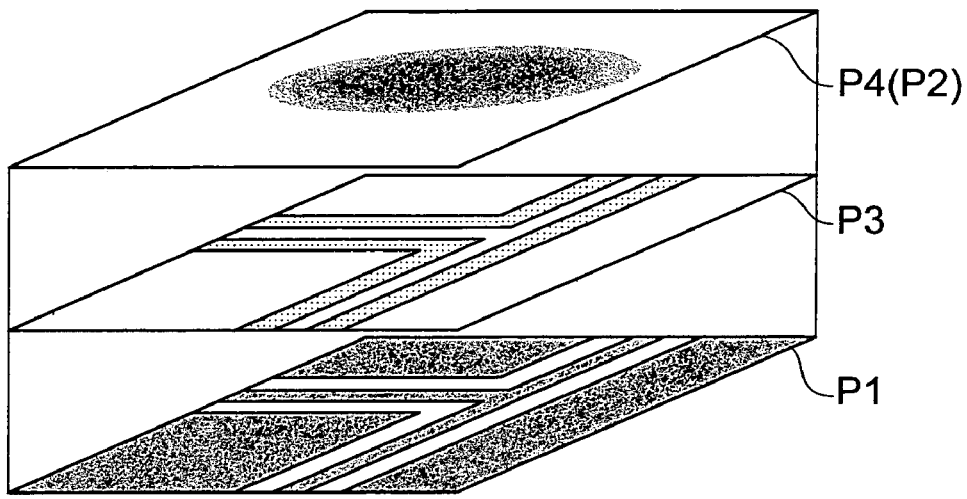
(b)
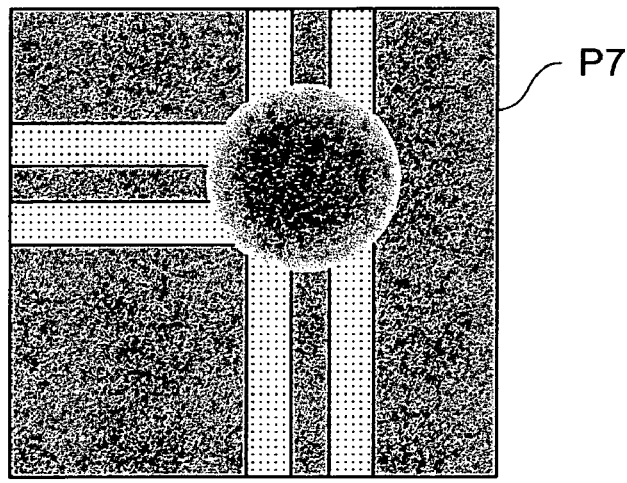

Fig.6
(a)
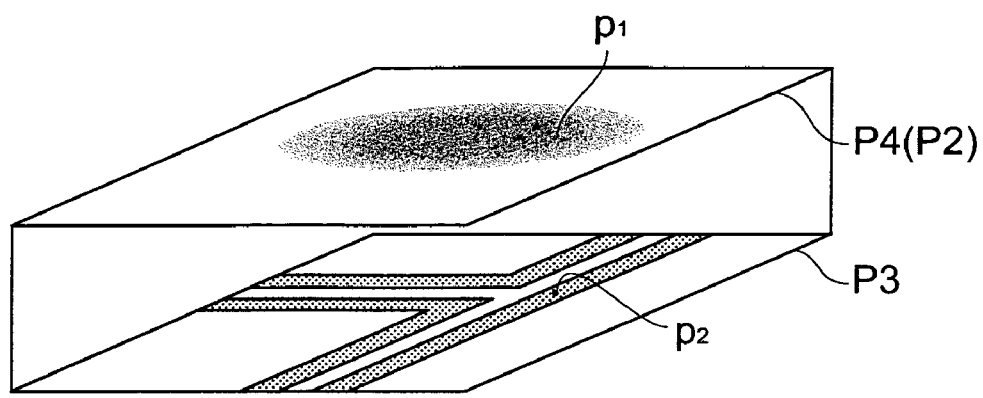
(b)
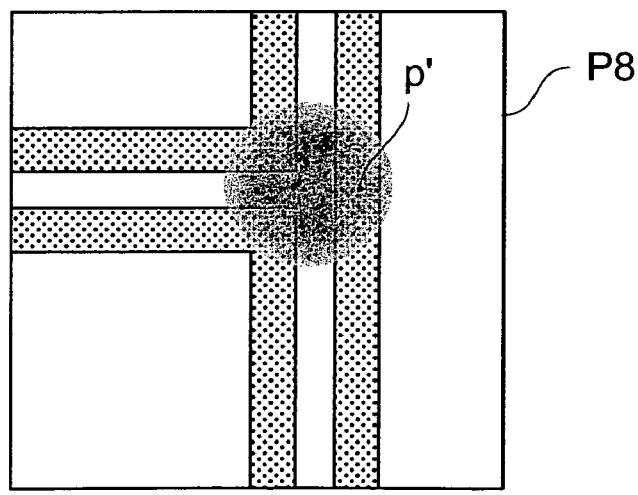

Fig.7
(a)
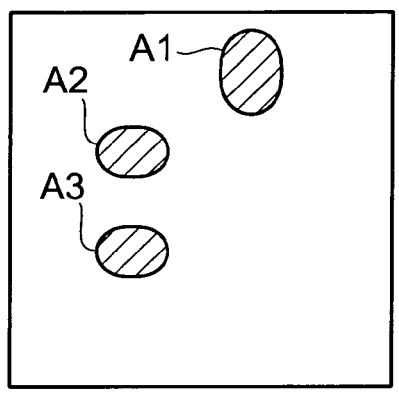
(d)
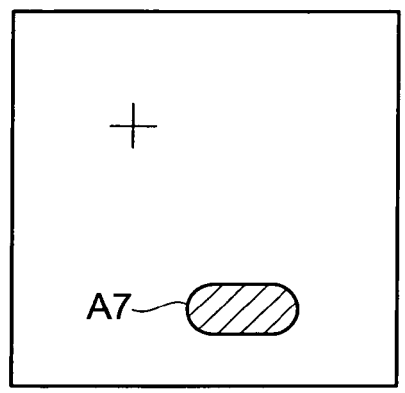
(b)
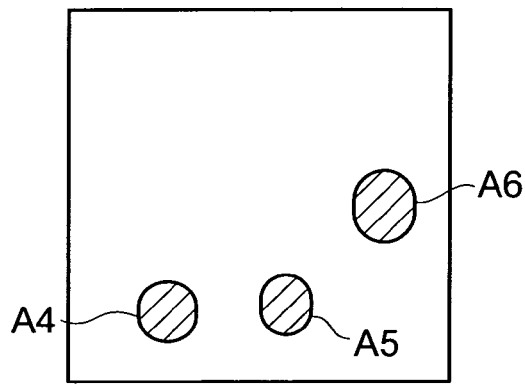
(e)
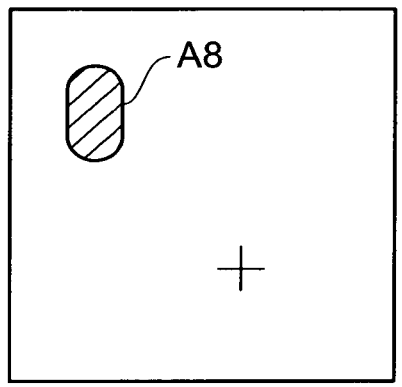
(c)
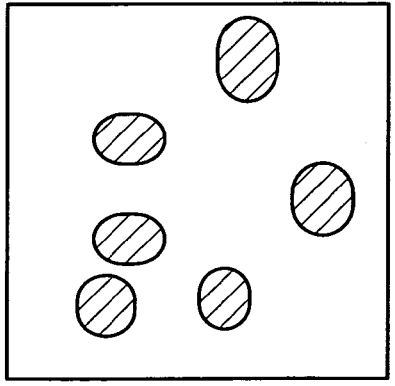
(f)
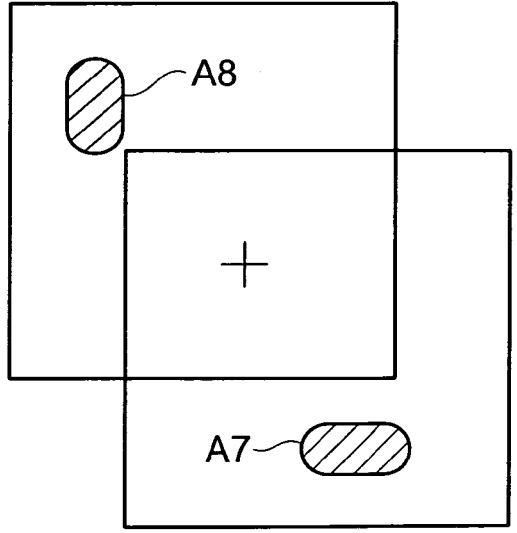

SEMICONDUCTOR FAILURE ANALYSIS APPARATUS, FAILURE ANALYSIS METHOD, FAILURE ANALYSIS PROGRAM, AND FAILURE ANALYSIS SYSTEM

BACKGROUND OF THE INVENTION

1. Field of the Invention

The present invention relates to a semiconductor failure analysis apparatus, failure analysis method, failure analysis program, and failure analysis system for analyzing a failure of a semiconductor device.

2. Related Background Art

The conventionally available semiconductor inspection apparatus for acquiring an observed image for analysis of failure of a semiconductor device include emission microscopes, OBIRCH apparatus, time-resolved emission microscopes, and so on. These inspection apparatus are able to analyze such a failure as a broken part in a semiconductor device by use of an emission image or OBIRCH image acquired as a failure observed image (e.g., reference is made to Patent Document 1: Japanese Patent Application Laid-Open No. 2003-86689 and to Patent Document 2: Japanese Patent Application Laid-Open No. 2003-303746).

SUMMARY OF THE INVENTION

In recent years, semiconductor devices as analysis objects in the semiconductor failure analysis have been miniaturized and integrated more and more, and it has become difficult to quickly perform the analysis of failure part by means of the aforementioned inspection apparatus or the like. In order to analyze the failure part of such a semiconductor device, it is thus essential to improve efficiency of analysis processing for estimating the failure part of the semiconductor device from an observed image.

The present invention has been accomplished in order to solve the above problem, and an object of the invention is to provide a semiconductor failure analysis apparatus, semiconductor failure analysis method, semiconductor failure analysis program, and semiconductor failure analysis system capable of efficiently performing an analysis of a failure of a semiconductor device with use of an observed image.

In order to achieve the above object, a semiconductor failure analysis apparatus according to the present invention is a semiconductor failure analysis apparatus for analyzing a failure of a semiconductor device, using an observed image thereof, comprising: (1) inspection information acquiring means for acquiring inspection information containing at least a pattern image being a normal observed image of the semiconductor device, as the observed image; (2) layout information acquiring means for acquiring layout information containing a layout image of the semiconductor device; (3) failure analyzing means for analyzing a failure of the semiconductor device with reference to the observed image; and (4) information display controlling means for letting display means display information about an analysis of the failure of the semiconductor device, (5) wherein the information display controlling means has superimposed image generating means for generating a superimposed image in which the pattern image and the layout image are superimposed, as an image of the semiconductor device to be displayed by the display means, and transmittance setting means for setting a transmittance of the layout image relative to the pattern image in the superimposed image.

A semiconductor failure analysis method according to the present invention is a semiconductor failure analysis method of analyzing a failure of a semiconductor device, using an observed image thereof, comprising: (a) an inspection information acquiring step of acquiring inspection information containing at least a pattern image being a normal observed image of the semiconductor device, as the observed image; (b) a layout information acquiring step of acquiring layout information containing a layout image of the semiconductor device; (c) a failure analyzing step of analyzing a failure of the semiconductor device with reference to the observed image; (d) an information displaying step of letting display means display information about an analysis of the failure of the semiconductor device; (e) a superimposed image generating step of generating a superimposed image in which the pattern image and the layout image are superimposed, as an image of the semiconductor device to be displayed by the display means; and (f) a transmittance setting step of setting a transmittance of the layout image relative to the pattern image in the superimposed image.

A semiconductor failure analysis program according to the present invention is a program for letting a computer execute a semiconductor failure analysis for analyzing a failure of a semiconductor device, using an observed image thereof, the program letting the computer execute: (a) an inspection information acquiring process for acquiring inspection information containing at least a pattern image being a normal observed image of the semiconductor device, as the observed image; (b) a layout information acquiring process of acquiring layout information containing a layout image of the semiconductor device; (c) a failure analyzing process of analyzing a failure of the semiconductor device with reference to the observed image; (d) an information displaying process of letting display means display information about an analysis of the failure of the semiconductor device; (e) a superimposed image generating process of generating a superimposed image in which the pattern image and the layout image are superimposed, as an image of the semiconductor device to be displayed by the display means; and (f) a transmittance setting process of setting a transmittance of the layout image relative to the pattern image in the superimposed image.

The above-described semiconductor failure analysis apparatus, failure analysis method, and failure analysis program are arranged to acquire the pattern image acquired as the observed image by the semiconductor inspection apparatus such as an emission microscope apparatus or OBIRCH apparatus, and the layout image of the semiconductor device. Then the superimposed image in which the pattern image and the layout image are superimposed is generated, and displayed by the display means. When the superimposed image of the pattern image and the layout image is used in this manner, it becomes easy to execute the failure analysis while relating the observed image and the layout image to each other, and the efficiency of the failure analysis is improved.

Furthermore, in the above configuration the transmittance of the layout image is variable relative to the pattern image, and superposition of the images is implemented with the transmittance being set to a desired value. This permits an observer to readily identify each of the pattern image, the layout image, and superposition thereof through appropriate setting of the transmittance. Therefore, it becomes feasible to securely and efficiently carry out the analysis of the failure of the semiconductor device with the use of the observed image. Where a failure observed image is acquired as another observed image along with the pattern image, the failure observed image, which is also the observed image as the pattern image is, can also be related to the layout image by relating the pattern image and the layout image to each other as described above.

A semiconductor failure analysis system according to the present invention is a system comprising: the semiconductor failure analysis apparatus described above; inspection information supplying means for supplying the inspection information to the semiconductor failure analysis apparatus; layout information supplying means for supplying the layout information to the semiconductor failure analysis apparatus; and the display means for displaying information about the analysis of the failure of the semiconductor device. The semiconductor failure analysis system of the above configuration enables us to securely and efficiently carry out the analysis of the failure of the semiconductor device with the use of the observed image, as described above.

The semiconductor failure analysis apparatus, failure analysis method, failure analysis program, and semiconductor failure analysis system according to the present invention are arranged to generate the superimposed image in which the pattern image and the layout image are superimposed, to make the transmittance of the layout image variable relative to the pattern image, and to effect superposition of the images with the transmittance being set to a desired value, whereby the observer is allowed to readily identify each of the pattern image, the layout image, and superposition thereof through appropriate setting of the transmittance. Therefore, it becomes feasible to securely and efficiently perform the analysis of the failure of the semiconductor device with the use of the observed image.

BRIEF DESCRIPTION OF THE DRAWINGS

FIG. 3 is a drawing schematically showing a semiconductor failure analysis method.

FIG. 4 is a schematic diagram showing an example of images of a semiconductor device displayed in a display device.

FIG. 5 is a schematic diagram showing another example of images of a semiconductor device displayed in a display device.

FIG. 6 is a schematic diagram showing another example of images of a semiconductor device displayed in a display device.

FIG. 7 is a drawing schematically showing acquisition of a failure observed image.

DESCRIPTION OF THE PREFERRED EMBODIMENTS

Figure 1:
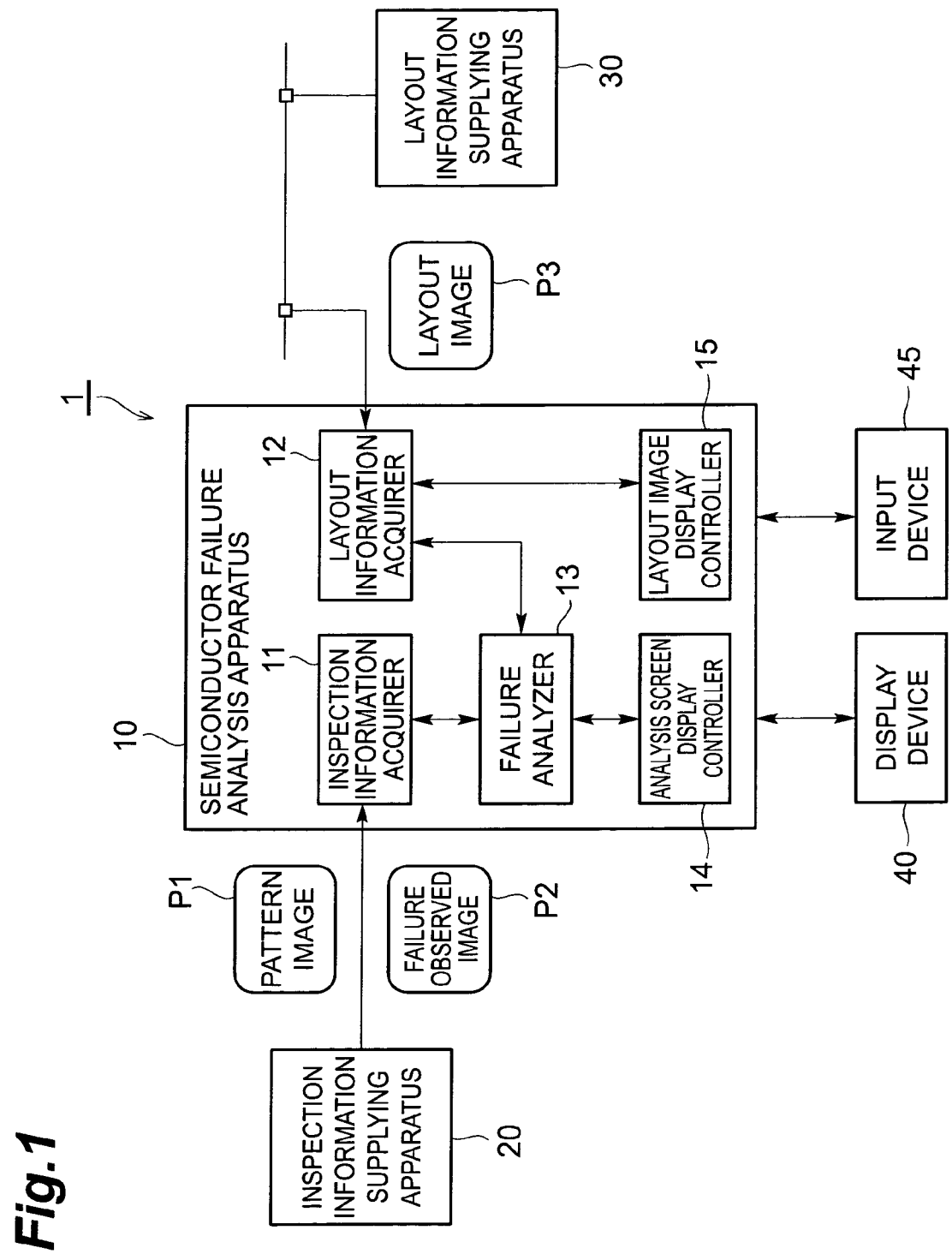
FIG. 1 is a block diagram showing a configuration of an embodiment of the failure analysis system incorporating the semiconductor failure analysis apparatus.

Preferred embodiments of the semiconductor failure analysis apparatus, failure analysis method, failure analysis program, and failure analysis system according to the present invention will be described below in detail with reference to the drawings. In the description of the drawings the same elements will be denoted by the same reference symbols, without redundant description. It is also noted that dimensional ratios in the drawings do not always agree with those in the description.

FIG. 1 is a block diagram schematically showing a configuration of an embodiment of the failure analysis system incorporating the semiconductor failure analysis apparatus according to the present invention. The present failure analysis system 1 is a system an analysis object of which is a semiconductor device and which is for carrying out an analysis of a failure with the use of an observed image thereof, and the system comprises a semiconductor failure analysis apparatus 10, an inspection information supplying apparatus 20, a layout information supplying apparatus 30, a display device 40, and an input device 45. Configurations of the semiconductor failure analysis apparatus 10 and failure analysis system 1 will be described below along with a semiconductor failure analysis method.

The semiconductor failure analysis apparatus 10 is an analysis apparatus for importing data necessary for the analysis of the failure of the semiconductor device and executing the analysis processing of the failure. The failure analysis apparatus 10 according to the present embodiment has an inspection information acquirer 11, a layout information acquirer 12, a failure analyzer 13, an analysis screen display controller 14, and a layout image display controller 15. Devices connected to the failure analysis apparatus 10 include the display device 40 for displaying information about the failure analysis, and the input device 45 used for instructions necessary for the failure analysis and for input of information necessary for the failure analysis.

Data to be used in the failure analysis executed in the failure analysis apparatus 10 is acquired by the inspection information acquirer 11 and by the layout information acquirer 12. The inspection information acquirer 11 acquires inspection information containing a pattern image P1 being a normal observed image of the semiconductor device, and a failure observed image P2 containing reaction information arising from a failure, obtained by conducting an inspection of the failure (inspection information acquiring step). The layout information acquirer 12 acquires layout information containing a layout image P3 indicating a configuration of nets or the like in the semiconductor device (layout information acquiring step).

In FIG. 1, the inspection information supplying apparatus 20 is connected to the inspection information acquirer 11, and the inspection information such as the pattern image P1 and the failure observed image P2 is supplied from the supplying apparatus 20 to the acquirer 11. This inspection information supplying apparatus 20 can be, for example, an emission microscope apparatus. In this case, the failure observed image P2 is an emission image. The inspection information supplying apparatus 20 can also be an OBIRCH apparatus. In this case, the failure observed image P2 is an OBIRCH image. Furthermore, the supplying apparatus 20 may also be any other type of semiconductor inspection apparatus than those.

Where the pattern image P1 and the failure observed image P2 are those preliminarily acquired by the semiconductor inspection apparatus, the inspection information supplying apparatus 20 is a data storage device storing those image data. The data storage device in this case may be one provided inside the failure analysis apparatus 10, or an external device. This configuration is useful in a case where observed images are taken and stored in advance by the semiconductor inspection apparatus and where software of failure analysis apparatus 10 is executed on another computer. In this case, works of the failure analysis can be performed as shared, without occupying the semiconductor inspection apparatus.

The pattern image P1 and the failure observed image P2 acquired by the semiconductor inspection apparatus such as the emission microscope apparatus or OBIRCH apparatus are acquired as images P1, P2 in a state in which the semiconductor device is mounted on a stage. For this reason, they are acquired as images aligned relative to each other.

On the other hand, the layout information supplying apparatus 30 is connected through a network to the layout information acquirer 12, and the layout information such as the layout image P3 is supplied from the supplying apparatus 30 to the acquirer 12. This layout information supplying apparatus 30 can be, for example, a workstation on which a CAD software application of a layout viewer to generate the layout image P3 from design information such as arrangement of elements and nets (wirings) constituting the semiconductor device, is running.

The failure analysis apparatus 10 is preferably configured to acquire the layout information other than the layout image P3, e.g., individual information of a plurality of nets contained in the semiconductor device, by performing communication with the layout information supplying apparatus 30 as occasion may demand. Alternatively, the failure analysis apparatus 10 may also be configured to load the information together with the layout image P3 from the layout information acquirer 12.

In the present embodiment the failure analysis apparatus 10 is provided with the layout image display controller 15. This layout image display controller 15 is constructed, for example, of an X Window Server and displays the layout image P3 drawn by the layout information supplying apparatus 30, in a predetermined display window or the like in the display device 40, separately from display of a superimposed image by the analysis screen display controller 14 described later (layout image displaying step). This improves the efficiency of the failure analysis using the images P1-P3. However, the layout image display controller 15 of this configuration does not always have to be provided if it is not necessary.

The pattern image P1, failure observed image P2, and layout image P3 acquired by the inspection information acquirer 11 and by the layout information acquirer 12 are fed to the failure analyzer 13. The failure analyzer 13 is an analyzing means for analyzing a failure of the semiconductor device with reference to the failure observed image P2 (failure analyzing step). This failure analyzer 13 makes reference to the other inspection information from the inspection information supplying apparatus 20 or to the layout information or the like from the layout information supplying apparatus 30, in addition to the failure observed image P2, as occasion may demand. In general, the essential function of the failure analyzer 13 is to perform the analysis of the failure of the semiconductor device with reference to the observed image.

The analysis screen display controller 14 is an information display controlling means for letting the display device 40 display information about the analysis of the failure of the semiconductor device (information displaying step). The information to be displayed in the display device 40 by the analysis screen display controller 14 includes, for example, an image of the semiconductor device as an analysis object, an analysis condition for the failure analysis executed for the semiconductor device, an analysis result of the failure of the semiconductor device by the failure analyzer 13, and so on.

Figure 2:
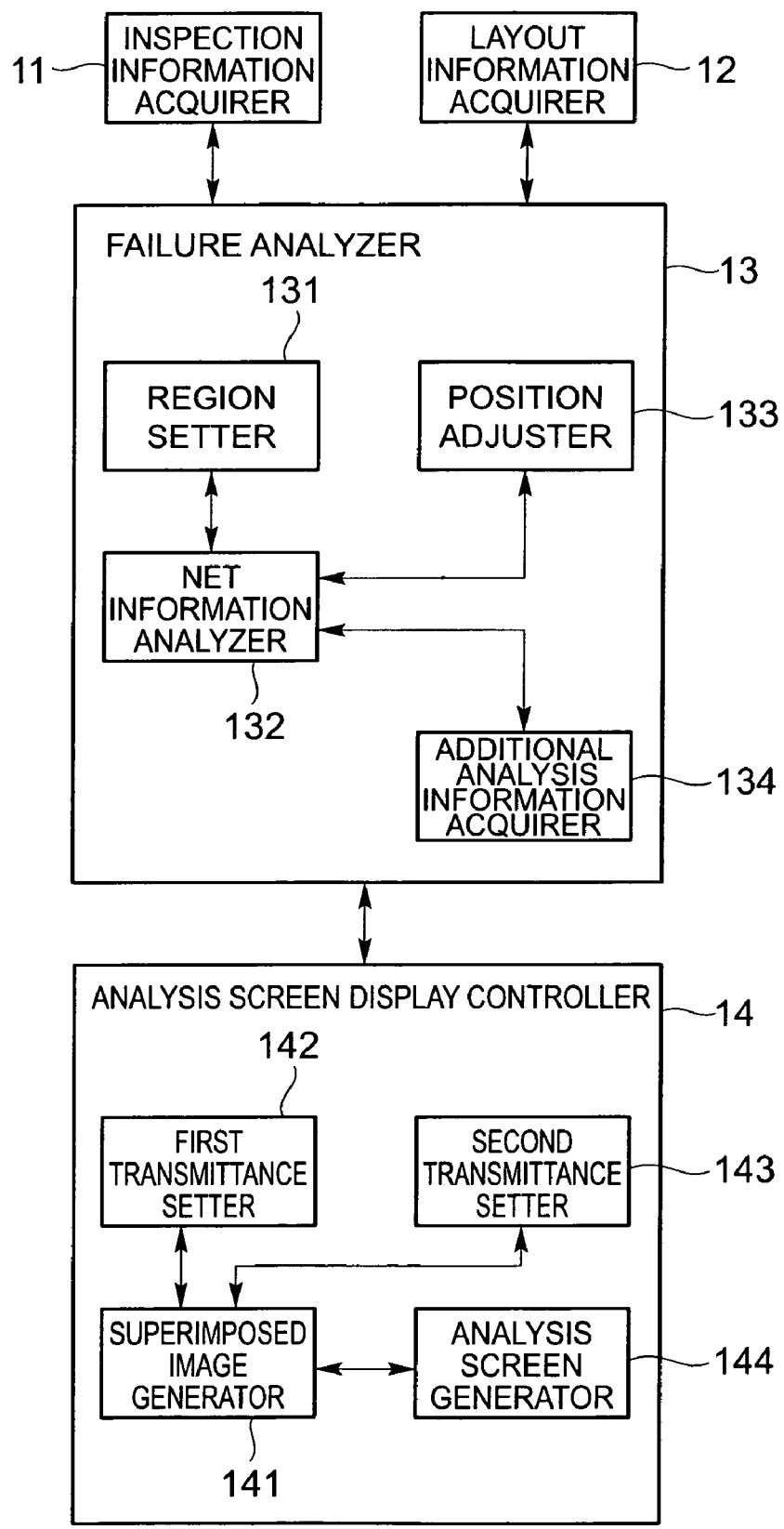
FIG. 2 is a block diagram showing a specific configuration of the semiconductor failure analysis apparatus shown in FIG. 1.

FIG. 2 is a block diagram showing a specific configuration of part of the semiconductor failure analysis apparatus 10 shown in FIG. 1. This figure shows specific configurations of the failure analyzer 13 and the analysis screen display controller 14 in the failure analysis apparatus 10.

First, the configuration of the failure analyzer 13 will be described. The failure analyzer 13 of the present embodiment has a region setter 131 and a net information analyzer 132. FIG. 3 is a drawing schematically showing a failure analysis method executed by the region setter 131 and net information analyzer 132.

The region setter 131 is a setting means for setting an analysis region in correspondence to reaction information in the image P2, with reference to the failure observed image P2, for the semiconductor device as an analysis object. Let us consider an emission image acquired by an emission microscope apparatus, as an example of the failure observed image P2. For example, in an example shown in (a) in FIG. 3, six emission regions A1-A6 (reaction regions arising from failures) exist as the reaction information referenced in the failure analysis, in an emission image. For this image, the region setter 131 sets six analysis regions B1-B6 corresponding to the emission regions, as shown in (b) in FIG. 3.

This setting of analysis regions is preferably manually carried out according to operator's input through the input device 45 using a keyboard, a mouse, and so on. Alternatively, the setting may be arranged to be automatically carried out in the region setter 131. There are no particular restrictions on the shape of the analysis regions thus set, but they are preferably set in the rectangular shape as shown in (b) in FIG. 3, in terms of easiness of analysis or the like. The analysis regions are preferably set wider than the reaction regions in the failure observed image P2, in consideration of positional accuracy of the stage on which the semiconductor device is mounted during inspection.

The net information analyzer 132 performs an analysis of a plurality of nets (wirings) included in the layout of the semiconductor device, with reference to the analysis regions set by the region setter 131. Specifically, it extracts a net passing an analysis region, from the plurality of nets. Where a plurality of analysis regions are set, the net information analyzer 132 acquires a passage count of each extracted net through the analysis regions.

In the example described above, as shown in (c) in FIG. 3, four nets C1-C4 are extracted as nets passing the analysis regions, with the six analysis regions B1-B6 set by the region setter 131. Among these nets C1-C4, the net C1 has the largest passage count of 3 through the analysis regions, the net C2 the passage count of 2, and each of the nets C3, C4 the passage count of 1.

In the analysis of such net information, it is preferable to execute the analysis by carrying out communication with the layout information supplying apparatus 30 through the layout information acquirer 12 as occasion may demand. An example of this configuration is such that the net information analyzer 132 is arranged to instruct the layout information supplying apparatus 30 to extract nets and to acquire the passage counts through the analysis regions, and to receive the result thereof.

The failure analyzer 13 of the present embodiment is provided with a position adjuster 133, corresponding to the configuration wherein the inspection information acquirer 11 acquires the pattern image P1 in addition to the failure observed image P2. The position adjuster 133 performs position adjustment between the observed image from the inspection information supplying apparatus 20 containing at least the pattern image P1, and the layout image P3 from the layout information supplying apparatus 30, with reference to the pattern image P1 and the layout image P3 (position adjustment step). This position adjustment can be performed, for example, by a method of designating three appropriate points in the pattern image P1, further designating three corresponding points in the layout image P3, and performing the position adjustment from coordinates of those points.

The failure analyzer 13 is provided with an additional analysis information acquirer 134. The additional analysis information acquirer 134 acquires additional analysis information about the failure of the semiconductor device acquired by another analysis method than the aforementioned analysis method by the region setter 131 and the net information analyzer 132, from an external device or the like. This additional analysis information acquired is referenced in combination with the analysis result acquired by the net information analyzer 132.

Next, the configuration of the analysis screen display controller 14 will be described. The analysis screen display controller 14 of the present embodiment has a superimposed image generator 141, a first transmittance setter 142, a second transmittance setter 143, and an analysis screen generator 144. FIGS. 4 to 6 are schematic diagrams showing examples of images of the semiconductor device generated by the superimposed image generator 141 and displayed in the display device 40.

The information such as the images necessary for the failure analysis in the failure analysis apparatus 10, or the information obtained as the analysis result is displayed as an analysis screen in the display device 40 by the analysis screen display controller 14 as occasion may demand. Particularly, in the present embodiment the superimposed image generator 141 generates a superimposed image (overlay image) in which the pattern image P1 and the layout image P3 are superimposed, as an image of the semiconductor device (superimposed image generating step). Then this superimposed image is displayed as information about the failure analysis in the display device 40.

FIG. 4 is a drawing showing an example of the superimposed image generated by the superimposed image generator 141, in which (a) in FIG. 4 shows a method of superimposing images and (b) in FIG. 4 the superimposed image generated. In this image example, the layout image P3, and the emission image P4 as the failure observed image P2 are superimposed in this order on the pattern image P1 to generate the superimposed image P6. The failure observed image P2 does not have to be limited to the emission image P4, but may be another failure observed image P2, e.g., OBIRCH image P5. As another example, the OBIRCH image P5 may be further superimposed in addition to the emission image P4, as indicated by dashed lines in (a) in FIG. 4. If the failure observed image P2 is unnecessary, only the layout image P3 may be superimposed on the pattern image P1 to generate the superimposed image.

In the configuration shown in FIG. 2, the superimposed image generator 141 is further provided with the first transmittance setter 142 and the second transmittance setter 143. The first transmittance setter 142 is a transmittance setting means for setting the transmittance of the layout image P3 relative to the pattern image P1 in the superimposed image P6 (transmittance setting step). The second transmittance setter 143 is a second transmittance setting means for setting the transmittance of the failure observed image P2 relative to the pattern image P1 and the layout image P3 in the superimposed image P6 (second transmittance setting step).

FIG. 5 is a drawing showing another example of the superimposed image generated by the superimposed image generator 141, in which (a) in FIG. 5 shows a method of superimposing images and (b) in FIG. 5 the superimposed image generated. In this image example, similar to the image example of FIG. 4, the pattern image P1, layout image P3, and failure observed image P2 are superimposed to generate the superimposed image P7. In this superimposed image P7, the transmittance of the layout image P3 superimposed on the pattern image P1 is set to 50%, relative to the pattern image P1 located below it, by the first transmittance setter 142.

FIG. 6 is a drawing showing still another example of the superimposed image generated by the superimposed image generator 141, in which (a) in FIG. 6 shows a method of superimposing images and (b) in FIG. 6 the superimposed image generated. In this image example, the pattern image P1 is omitted from the illustration, but the pattern image P1, layout image P3, and failure observed image P2 are superimposed to generate the superimposed image P8 as in the case of the image example of FIG. 4. In this superimposed image P8, the transmittance of the failure observed image P2 superimposed on the pattern image P1 and the layout image P3 is set to 50%, relative to the pattern image P1 and layout image P3 located below it, by the second transmittance setter 143.

The transmittances of the images by the first transmittance setter 142 and by the second transmittance setter 143 are preferably manually set according to operator's input through the input device 45 using a keyboard, a mouse, and so on. Alternatively, the transmittance setters 142, 143 may be arranged to automatically carry out the transmittance setting according to a predetermined condition.

The analysis screen display controller 14 may be arranged to make the display device 40 display the analysis result of the failure of the semiconductor device by the failure analyzer 13 according to need, as described above. The display of the analysis result is implemented, for example, by a configuration of displaying information about nets extracted by the net information analyzer 132 and passage counts of the nets through the analysis regions. This display of the analysis result may be implemented, for example, by displaying an image including the analysis regions and nets as shown in (c) in FIG. 3, or by displaying a net list or the like to display a list of names of nets extracted, and passage counts of the nets through the analysis regions. In the case of an image including the analysis regions and nets, as shown in (c) in FIG. 3, the extracted nets may be indicated by highlight display on the layout image. A variety of specific display methods may be applied; e.g., where an extracted net is selected by manipulation of a mouse or the like, an analysis region through which the net passes is displayed by a different color.

The analysis screen display controller 14 shown in FIG. 2 is further provided with the analysis screen generator 144. The analysis screen generator 144 is a generating means for generating an analysis screen (e.g., analysis window screen) including information about the failure analysis of the semiconductor device, as a screen to be displayed in the display device 40 (analysis screen generating step). The analysis screen displayed in the display device 40 will be specifically described later.

The effects of the semiconductor failure analysis apparatus, failure analysis method, and failure analysis system according to the above embodiment will be described below.

The semiconductor failure analysis apparatus 10 shown in FIG. 1, and the failure analysis method are arranged to acquire the pattern image P1 acquired as an observed image by the semiconductor inspection apparatus and the layout image P3 containing the information about the arrangement of nets and others of the semiconductor device, for the semiconductor device as an analysis object. Then the superimposed image generator 141 of the analysis screen display controller 14 generates the superimposed image in which the pattern image P1 and the layout image P3 are superimposed, and it is displayed in the display device 40. The use of the superimposed image of the pattern image and the layout image in this manner facilitates execution of the failure analysis while relating the observed image and the layout image to each other, and improves the efficiency thereof.

Namely, the failure analysis of the semiconductor device executed in the failure analysis apparatus 10 sometimes requires execution of the analysis while relating the observed image such as the pattern image P1, to the layout image P3. In such cases, the use of the superimposed image generated as described above facilitates execution of the failure analysis while relating the observed image to the layout image P3, and improves the efficiency thereof.

Furthermore, in the above configuration the transmittance of the layout image P3 is variable relative to the pattern image P1, and the superposition of images is carried out while the first transmittance setter 142 sets the transmittance to a desired value. This permits the observer to readily identify each of the information about the pattern image P1, the information about the layout image P3, and the information about superposition thereof (correspondence) in the superimposed image displayed in the display device 40, through appropriate setting or change of the transmittance. Therefore, the use of the foregoing superimposed image enables secure and efficient execution of the analysis of the failure of the semiconductor device with the use of the observed image.

Where the failure observed image P2 is acquired as another observed image together with the pattern image P1, the failure observed image P2, which is also the observed image as the pattern image P1 is, and which is an image aligned in position with the pattern image P1, can also be related to the layout image P3 at the same time as the pattern image P1 is related to the layout image P3 as described above. In the failure analysis with a physical analyzer using an electron beam or ion beam (e.g., failure analysis with a transmission electron microscope), the failure can be observed just by superposition of the pattern image P1 and layout image P3.

The failure analysis system 1 composed of the above-described semiconductor failure analysis apparatus 10, inspection information supplying apparatus 20, layout information supplying apparatus 30, and display device 40 substantializes a semiconductor failure analysis system capable of securely and efficiently carrying out the analysis of the failure of the semiconductor device with the use of the observed image.

In the example shown in FIG. 4, the failure observed image P2 is further superimposed together with the pattern image P1 and layout image P3 to generate the superimposed image P6. When the system is configured in this configuration wherein the failure observed image P2 is further superimposed in addition to the pattern image P1 and the layout image P3, wherein the transmittance of the failure observed image P2 is made variable relative to the pattern image P1 and layout image P3, wherein the second transmittance setter 143 sets the transmittance to a desired value, and wherein the superposition of images is carried out based thereon, it becomes feasible to readily identify each of the information about the images P1-P3 and superposition thereof (correspondence) through appropriate setting or change of the transmittance, and to further improve the efficiency of the failure analysis.

For example, the use of this superimposed image permits us to readily identify where an abnormal part (e.g., an emission part in an emission image) on the failure observed image P2 is located on the layout of the semiconductor device.

Concerning the superposition of images P1-P3 in the superimposed image, where the pattern image P1 is superimposed with the layout image P3, it is preferable to superimpose the layout image P3 on the pattern image P1. Namely, the pattern image P1 as a normal observed image of the semiconductor device is normally an image without any pixels that can be handled as transparent elements. On the other hand, the layout image P3 includes a reduced number of pixels that can be handled as transparent elements because of the configuration of the layout in which a number of nets exist, but there are some pixels that can be handled as transparent elements because of regularity of the layout or the like. Therefore, when the superimposed image is generated by locating the pattern image P1 on the lower side and the layout image P3 on the upper side as described above, the lower pattern image P1 can be recognized through the pixels that can be handled as transparent elements in the layout image P3.

Where the failure observed image P2 is superimposed with the pattern image P1 and layout image P3, it is preferable to superimpose the failure observed image P2 on the pattern image P1 and the layout image P3. Namely, the failure observed image P2 such as the emission image P4 or OBIRCH image P5 normally includes data pixels localized, and has a larger number of pixels that can be handled as transparent elements than the pattern image P1 and the layout image P3. Therefore, when the superimposed image is generated by locating the pattern image P1 and layout image P3 on the lower side and the failure observed image P2 on the upper side as described above, it becomes easier to achieve cross-relation or the like among the pattern image P1, failure observed image P2, and layout image P3.

It is, however, noted that the orders of superposition of the images P1-P3 in the superimposed image are not limited to the above-described orders, but may be set to various orders according to specific characteristics of the respective images or the like.

Let us explain an example of a specific generating method (transmittance setting method) for generating the superimposed image in the superimposed image generator 141, using the superimposed image P8 of the layout image P3 and the failure observed image P2 shown in FIG. 6. Let $p_1$ be a point on the failure observed image P2 corresponding to a point p' on the superimposed image P8, $p_2$ be a point on the layout image P3 corresponding to the point p', r, g, and b be RGB color elements at each point, and T be the transmittance of the failure observed image P2 relative to the layout image P3, and then each of the RGB color elements at the point p' on the superimposed image P8 is represented as follows.

$$p'(r)=T \cdot p_2(r)+(1-T) \cdot p_1(r)$$

$$p'(g)=T \cdot p_2(g)+(1-T) \cdot p_1(g)$$

$$p'(b)=T \cdot p_2(b)+(1-T) \cdot p_1(b)$$

In this manner, the superimposed image can be suitably generated by obtaining the data elements p' at each point in the superimposed image, from the data elements $p_2$, $p_1$ of the images to be superimposed. For example, as seen from the above equations, when the transmittance T is equal to 0, the superimposed image becomes the failure observed image P2. When the transmittance T is equal to 1, the superimposed image becomes the layout image P3. When the transmittance T is a value between 0 and 1, the superimposed image becomes an image in which the layout image P3 is seen below and through the failure observed image P2, as shown in (b) in FIG. 6.

The failure analysis apparatus 10 of the present embodiment is arranged to set an analysis region corresponding to reaction information arising from a failure in the failure observed image P2, and to extract a net passing the analysis region out of the nets constituting the semiconductor device, to perform the failure analysis. In this case, where the analysis region is suitably set, a net with a high possibility of failure (suspect failure net) can be estimated by extracting a net passing the analysis region, and the failure analysis can be efficiently executed. It is, however, noted that specific analysis methods in the failure analyzer 13 can be a variety of methods other than the above described method. In general, the essential function of the failure analyzer 13 is to carry out the analysis of the failure of the semiconductor device with reference to the observed image. The reaction information caused by a failure in the failure observed image P2 includes not only a case where the reaction part itself is a failure part, but also a portion where reaction occurs because of another failure part (e.g., failure net), and it is thus preferable to use an analysis method taking account of it.

The emission image was exemplified as the failure observed image P2 in (a) in FIG. 3, but the failure observed image P2 may also be another observed image, e.g., an OBIRCH image as described above. The failure observed image can be an image obtained by a single observation under a single condition, but the failure observed image is not limited to it; for example, as shown in FIG. 7, the failure observed image can be a superimposed image as shown in (c) in FIG. 7 of a failure observed image of (a) in FIG. 7 acquired under a first condition and a failure observed image of (b) in FIG. 7 acquired under a second condition different from the first condition.

In the acquisition of the failure observed image under the second condition described above, it can also be contemplated that an observation position is changed from that in the first condition (e.g., a position or range in the failure observed image is changed), as shown in (d) and (e) in FIG. 7. In such cases, as shown in (f) in FIG. 7, it is preferable to implement the superposition of images in consideration of the change information of the observation position. Another possible method is to store the analysis result obtained under the first condition, into a storage means and to add the analysis result obtained under the second condition. By performing these multiple times, it is feasible to improve the efficiency and certainty of the failure analysis, e.g., to make a distribution of passage frequencies of nets more distinguished.

In the above embodiment the failure analysis apparatus 10 is configured so that the position adjuster 133 of the failure analyzer 13 performs the image position adjustment with reference to the pattern image P1 and the layout image P3. When the position adjustment with the layout image P3 is carried out using the pattern image P1 as in this configuration, it is feasible to improve the accuracy of the analysis of the failure of the semiconductor device with the use of the observed image. The superimposed image of the pattern image P1 and the layout image P3 described above is also effective in execution of this position adjustment. Particularly, where the failure observed image P2 is acquired as another observed image together with the pattern image P1, the aforementioned position adjustment is effective because the pattern image P1 is acquired in a state in which it is aligned in position with the failure observed image P2.

In the above embodiment the failure analysis apparatus 10 is configured so that the additional analysis information acquirer 134 of the failure analyzer 13 acquires the additional analysis information as to the failure of the semiconductor device acquired by another analysis method, e.g., information of a suspect failure net. By referencing such additional analysis information, it is feasible to further improve the accuracy of the analysis of the failure of the semiconductor device.

The processing corresponding to the failure analysis method executed in the semiconductor failure analysis apparatus 10 shown in FIG. 1 can be implemented by a semiconductor failure analysis program for letting a computer execute the semiconductor failure analysis. For example, the failure analysis apparatus 10 can be constructed of a CPU for executing each of software programs necessary for the processing of semiconductor failure analysis, a ROM storing the software programs, and a RAM temporarily storing data during execution of the programs. The aforementioned failure analysis apparatus 10 can be substantialized by letting the CPU execute a predetermined failure analysis program in this configuration.

The program for letting the CPU execute each of processes for the semiconductor failure analysis can be recorded in a computer-readable recording medium and distributed in that form. Such recording media include, for example, magnetic media such as hard disks and flexible disks, optical media such as CD-ROM and DVD-ROM, magnetooptic media such as floptical disks, or hardware devices such as RAM, ROM, and semiconductor nonvolatile memories specially arranged to execute or store program commands.

Figure 8:
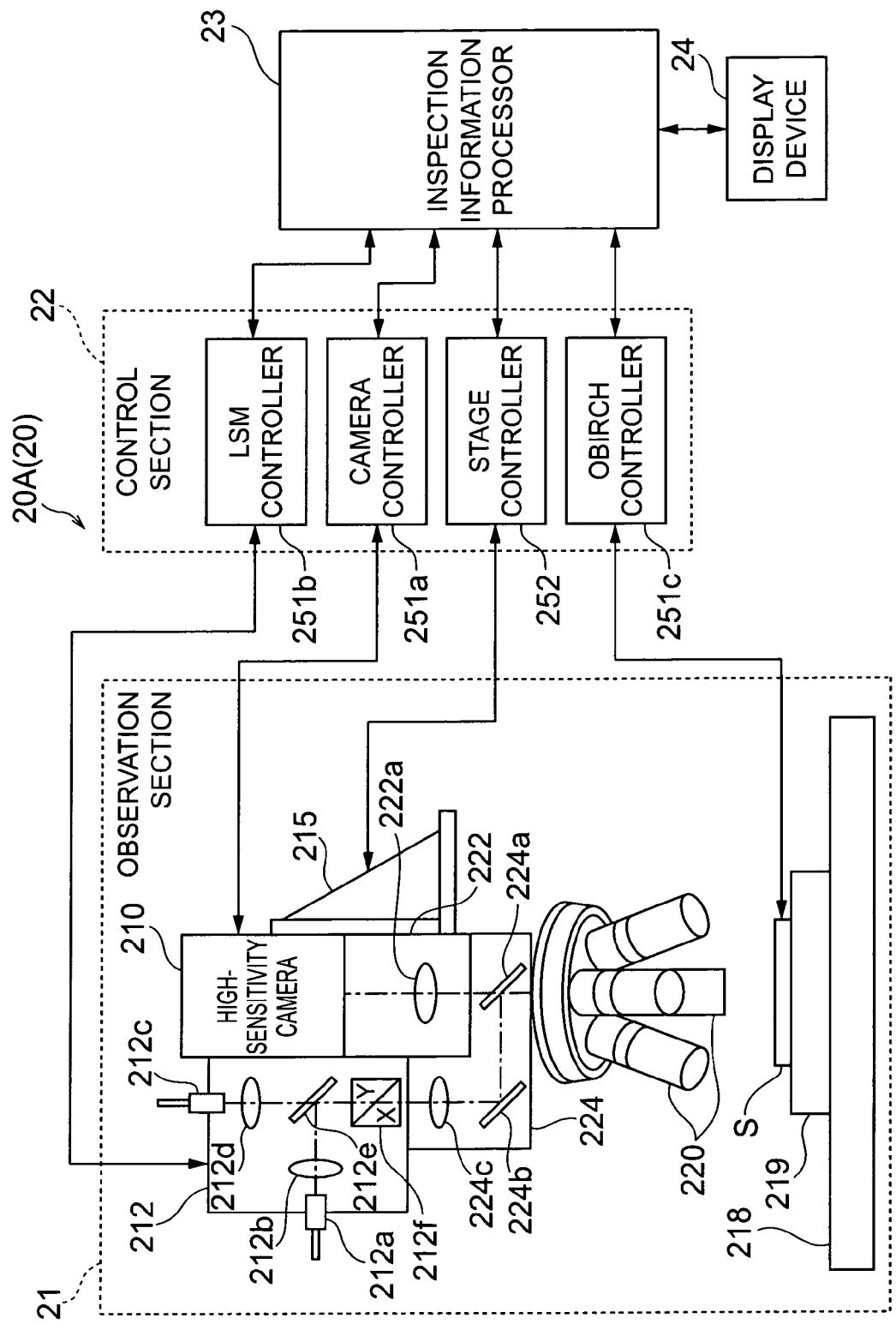
FIG. 8 is a configuration diagram showing an example of semiconductor inspection apparatus.
Figure 9:
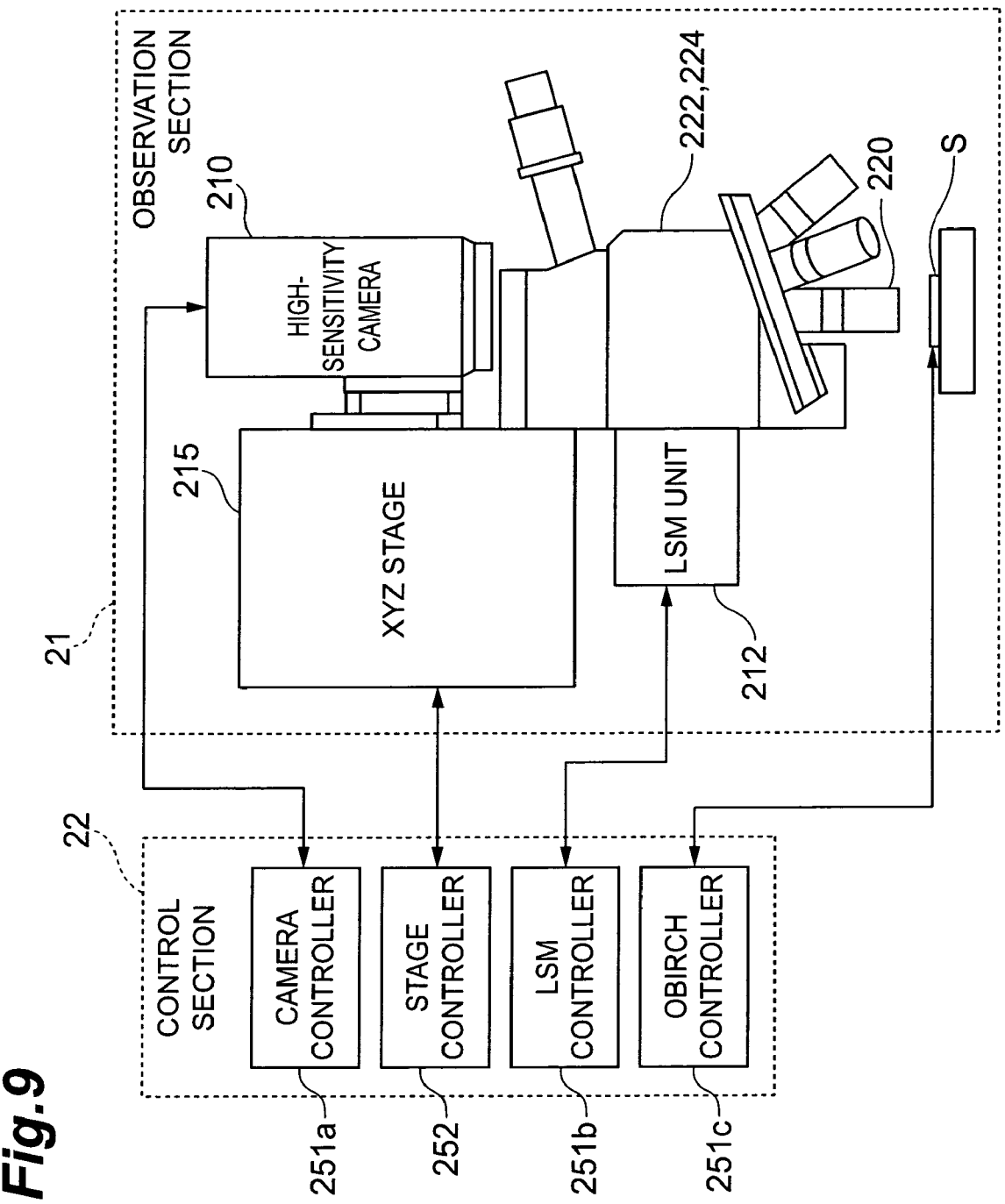
FIG. 9 is a configuration diagram as a side view of the semiconductor inspection apparatus shown in FIG. 8.

FIG. 8 is a configuration diagram showing an example of semiconductor inspection apparatus which can be applied as the inspection information supplying apparatus 20 shown in FIG. 1. FIG. 9 is a configuration diagram as a side view of the semiconductor inspection apparatus shown in FIG. 8.

The semiconductor inspection apparatus 20A according to the present configuration example comprises an observation section 21 and a control section 22. A semiconductor device S as an inspection object (analysis object to be analyzed by the failure analysis apparatus 10) is mounted on a stage 218 provided in the observation section 21. In the present configuration example, the apparatus is further provided with a test fixture 219 for applying an electric signal or the like necessary for the failure analysis to the semiconductor device S. The semiconductor device S is arranged, for example, so that a back face thereof faces an objective lens 220.

The observation section 21 has a high-sensitivity camera 210 set in a dark box, a laser scan optic (LSM: Laser Scanning Microscope) unit 212, optical systems 222, 224, and an XYZ stage 215. Among these, the camera 210 and LSM unit 212 are image acquiring means for acquiring an observed image of the semiconductor device S (pattern image P1 or failure observed image P2).

The optical systems 222, 224, and the objective lens 220 disposed on the semiconductor device S side of the optical systems 222, 224 constitute a lightguide optical system for guiding an image (optical image) from the semiconductor device S to the image acquiring means. In the present configuration example, as shown in FIGS. 8 and 9, a plurality of objective lenses 220 having their respective magnifications different from each other are arranged so as to be switchable from one to another. The test fixture 219 is an inspecting means for performing an inspection for the failure analysis of the semiconductor device S. The LSM unit 212 also has a function as an inspecting means, as well as the function as the aforementioned image acquiring means.

The optical system 222 is a camera optical system for guiding light from the semiconductor device S incident thereto through the objective lens 220, to the camera 210. The camera optical system 222 has an imaging lens 222a for forming an image enlarged at a predetermined magnification by the objective lens 220, on a light-receiving surface inside the camera 210. A beam splitter 224a of the optical system 224 is interposed between the objective lens 220 and the imaging lens 222a. The high-sensitivity camera 210 to be used is, for example, a cooled CCD camera or the like.

In this configuration, light from the semiconductor device S as a failure analysis object is guided through the optical system including the objective lens 220 and the cameral optical system 222, to the camera 210. Then the camera 210 acquires an observed image such as the pattern image P1 of the semiconductor device S. It is also possible to acquire an emission image being a failure observed image P2 of the semiconductor device S. In this case, light generated from the semiconductor device S in a state in which a voltage is applied thereto by the test fixture 219 is guided through the optical system to the camera 210, and the camera 210 acquires an emission image.

The LSM unit 212 has a laser input optical fiber 212a for emitting an infrared laser beam, a collimator lens 212b for collimating the laser beam emitted from the optical fiber 212a, a beam splitter 212e for reflecting the laser beam collimated by the lens 212b, and an XY scanner 212f for emitting the laser beam reflected by the beam splitter 212e, to the semiconductor device S side, while scanning it in XY directions.

The LSM unit 212 further has a condenser lens 212d for condensing light incident thereto from the semiconductor device S side through the XY scanner 212f and transmitted by the beam splitter 212e, and a detection optical fiber 212c for detecting the light condensed by the condenser lens 212d.

The optical system 224 is an optical system for the LSM unit which guides light between the semiconductor device S and objective lens 220, and the XY scanner 212f of the LSM unit 212. The optical system 224 for the LSM unit has a beam splitter 224a for reflecting part of light incident thereto from the semiconductor device S through the objective lens 220, a mirror 224b for changing an optical path of the light reflected by the beam splitter 224a, into an optical path directed toward the LSM unit 212, and a lens 224c for condensing the light reflected by the mirror 224b.

In this configuration, the infrared laser beam emitted from a laser light source through the laser input optical fiber 212a passes the lens 212b, beam splitter 212e, XY scanner 212f, optical system 224, and objective lens 220 to irradiate the semiconductor device S.

Reflectively scattered light of this incident beam from the semiconductor device S reflects: a circuit pattern provided in the semiconductor device S. The reflected light from the semiconductor device S passes through an optical path opposite to that of the incident beam to reach the beam splitter 212e, and passes through the beam splitter 212e. Then the light passing through the beam splitter 212e is incident through the lens 212d into the detection optical fiber 212c to be detected by a photodetector connected to the detection optical fiber 212c.

An intensity of the light detected through the detection optical fiber 212c by the photodetector is an intensity reflecting the circuit pattern provided in the semiconductor device S, as described above. Therefore, as the area on the semiconductor device S is scanned by X-Y scanning with the infrared laser beam by the XY scanner 212f, the pattern image P1 or the like of the semiconductor device S can be acquired as a clear image.

The control section 22 has a camera controller 251a, an LSM controller 251b, an OBIRCH controller 251c, and a stage controller 252. Among these, the camera controller 251a, LSM controller 251b, and OBIRCH controller 251c constitute an observation controlling means for controlling operations of the image acquiring means, inspection means, etc. in the observation section 21, thereby controlling the acquisition of the observed image of the semiconductor device S, the setting of observation conditions, etc. executed in the observation section 21.

Specifically, the camera controller 251a and LSM controller 251b control the operations of the high-sensitivity camera 210 and the LSM unit 212, respectively, to control the acquisition of the observed image of the semiconductor device S. The OBIRCH controller 251c is a controller for acquiring an OBIRCH (Optical Beam Induced Resistance Change) image which can be used as a failure observed image, and extracts an electric current change or the like in the semiconductor device S occurring during the scanning with the laser beam.

The stage controller 252 controls the operation of the XYZ stage 215 in the observation section 21, thereby controlling setting of an observed portion in the semiconductor device S as an inspection portion by the present inspection apparatus 20A, position adjustment thereof, focusing, and so on.

An inspection information processor 23 is provided for these observation section 21 and control section 22. The inspection information processor 23 performs such processing as data collection of the observed image of the semiconductor device S acquired in the observation section 21, supply of inspection information including the pattern image P1 and failure observed image P2, to the failure analysis apparatus 10 (cf. FIG. 1), and so on. It is also possible to adopt a configuration wherein a display device 24 is connected to this inspection information processor 23 as occasion may demand. It is noted that FIG. 9 is illustrated without illustration of the inspection information processor 23 and the display device 24.

Specific examples of the display method of the superimposed image of the semiconductor device in the display device 40 by the semiconductor failure analysis apparatus 10 shown in FIG. 1, the failure analysis method by the failure analysis apparatus 10, etc. will be described with examples of an analysis screen (analysis window) displayed in the display device 40 by the analysis screen display controller 14. Such an analysis screen is generated by the analysis screen generator 144 in the configuration shown in FIG. 2.

Figure 10:
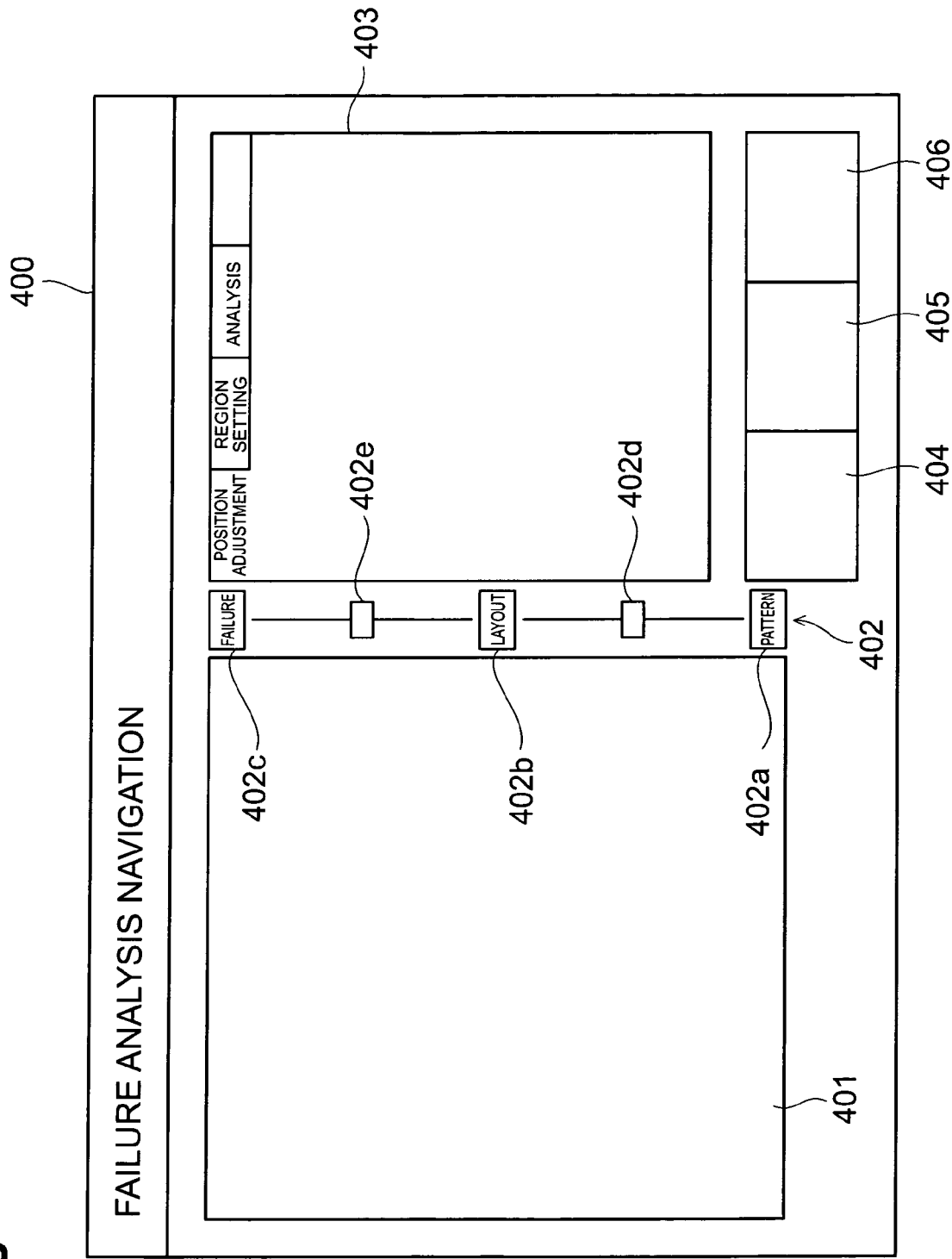
FIG. 10 is a configuration diagram showing an example of an analysis window displayed in a display device.

FIG. 10 is a configuration diagram showing an example of an analysis window (failure analysis navigation window) displayed in the display device 40. This analysis window 400 is an analysis screen used for the display of the superimposed image generated by the superimposed image generator 141 and for the setting of the transmittance of the image by the transmittance setters 142, 143 in the present example.

Specifically, the analysis window 400 has an image display region 401 used for display of each image to be used in the failure analysis, such as the pattern image P1, failure observed image P2, or layout image P3 of the semiconductor device, which is located on the left side of the screen, and a display adjustment region 402 for giving instructions for adjustment of a display condition for the image in the image display region 401, which is located in the center of the screen.

Regions provided on the right side of the screen in the analysis window 400 are an analysis operation region 403 used for instructions and entry of information necessary for the analysis process carried out in the failure analyzer 13, an inspection information acquisition operation region 404 for controlling acquisition of information from the inspection information supplying apparatus 20, a layout information acquisition operation region 405 for controlling acquisition of information from the layout information supplying apparatus 30, and a communication operation region 406 for controlling a communication state with the supplying apparatus 20, 30. The analysis process executed in the failure analysis apparatus 10 is controlled using these regions 403-406 by an operator.

As described above, the analysis window 400 shown in FIG. 10 is constructed with the image display region 401 capable of displaying the superimposed image generated by the superimposed image generator 141, and with the analysis operation region 403 used in the operations for the analysis of failure carried out in the failure analyzer 13. Use of the analysis screen of this configuration enhances operator's convenience in execution of the failure analysis by means of the failure analysis apparatus 10. The image of the semiconductor device to be displayed in the image display region 401 may be another image than the superimposed image as occasion may demand.

This analysis window 400 permits the operator to adjust the condition for generation of the superimposed image, including the transmittance of the image, by the display adjustment region 402 provided in the center of the screen. Specifically, the following three display switch buttons are provided in the order named from bottom in this display adjustment region 402: a pattern image display switch button 402a for switching the display of the pattern image P1 on or off; a layout image display switch button 402b for switching the display of the layout image P3 on or off; and a failure observed image display switch button 402c for switching the display of the failure observed image P2 on or off.

Furthermore, the display adjustment region 402 is provided with a first transmittance setting tab 402d for setting of the transmittance of the layout image P3 relative to the pattern image P1, between the display switch buttons 402a, 402b. The setting of the transmittance in the first transmittance setter 142 of the analysis screen display controller 14 is implemented by manipulating this setting tab 402d. The display adjustment region 402 is also provided with a second transmittance setting tab 402e for setting of the transmittance of the failure observed image P2 relative to the pattern image P1 and the layout image P3, between the display switch buttons 402b, 402c. The setting of the transmittance in the second transmittance setter 143 of the analysis screen display controller 14 is implemented by manipulating this setting tab 402e.

As the analysis screen is provided with the display adjustment region 402 having the display switch buttons 402a-402c and the transmittance setting tabs 402d, 402e as described above, the operator is allowed to suitably and readily control the generation condition for the superimposed image in the superimposed image generator 141 in accordance with an operator's need. The analysis screen may be arranged in a variety of specific configurations other than the configuration example shown in FIG. 10. For example, the display adjustment region 402 may be provided with only the transmittance setting tabs 402d, 402e, without the display switch buttons 402a-402c.

Figure 11:
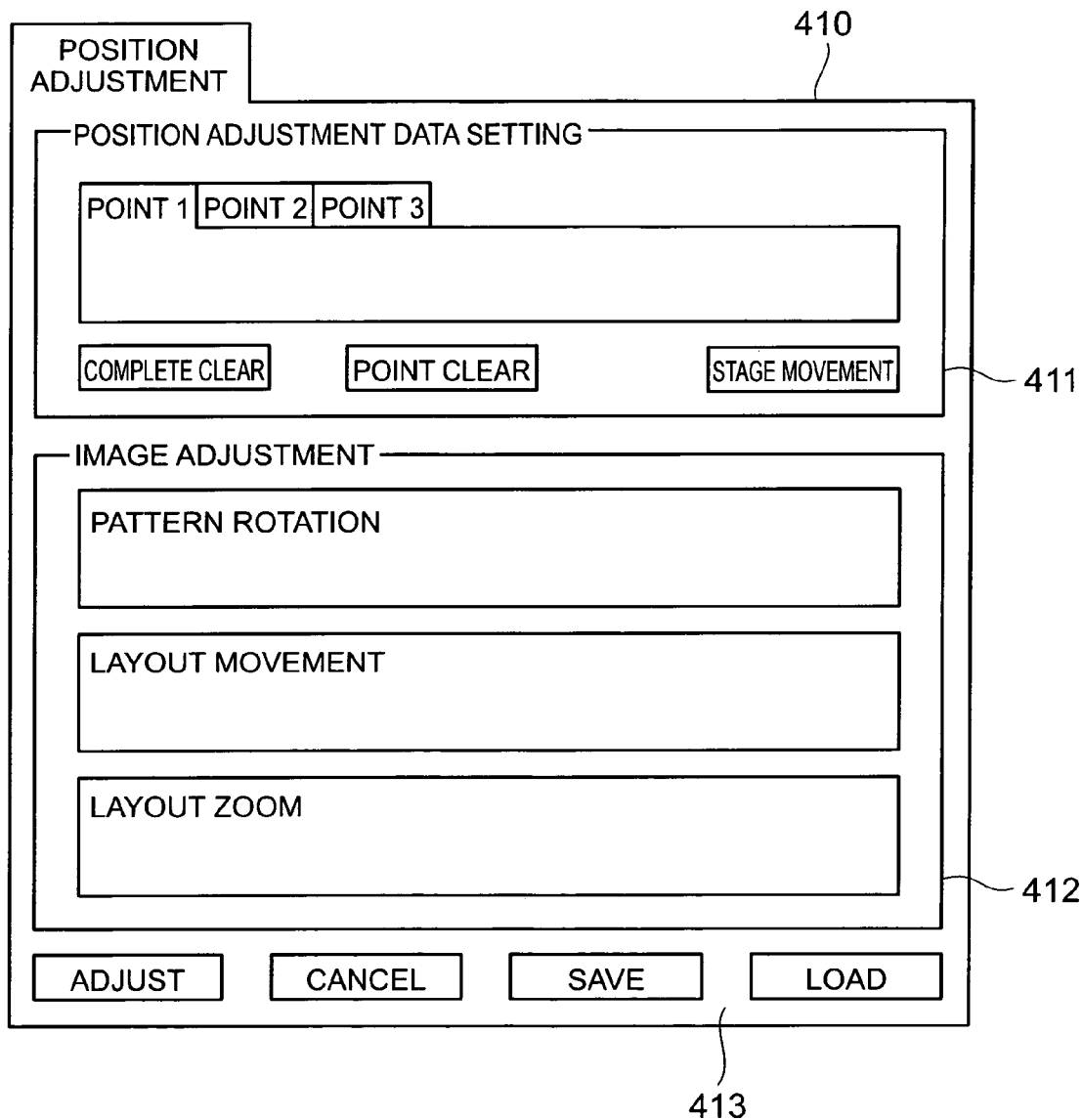
FIG. 11 is a configuration diagram showing an example of an operation screen displayed in an analysis operation region.
Figure 12:
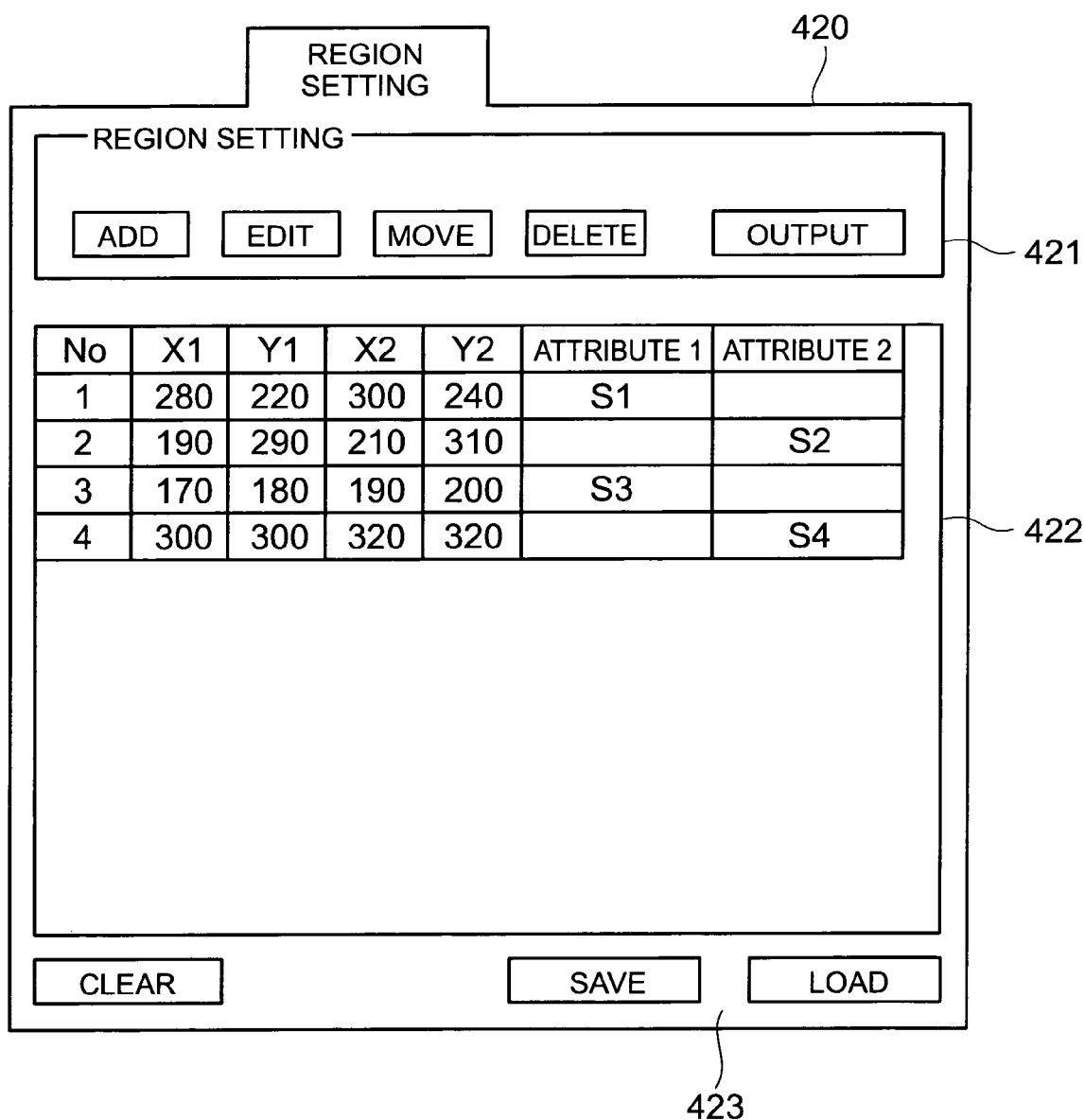
FIG. 12 is a configuration diagram showing another example of an operation screen displayed in an analysis operation region.
Figure 13:
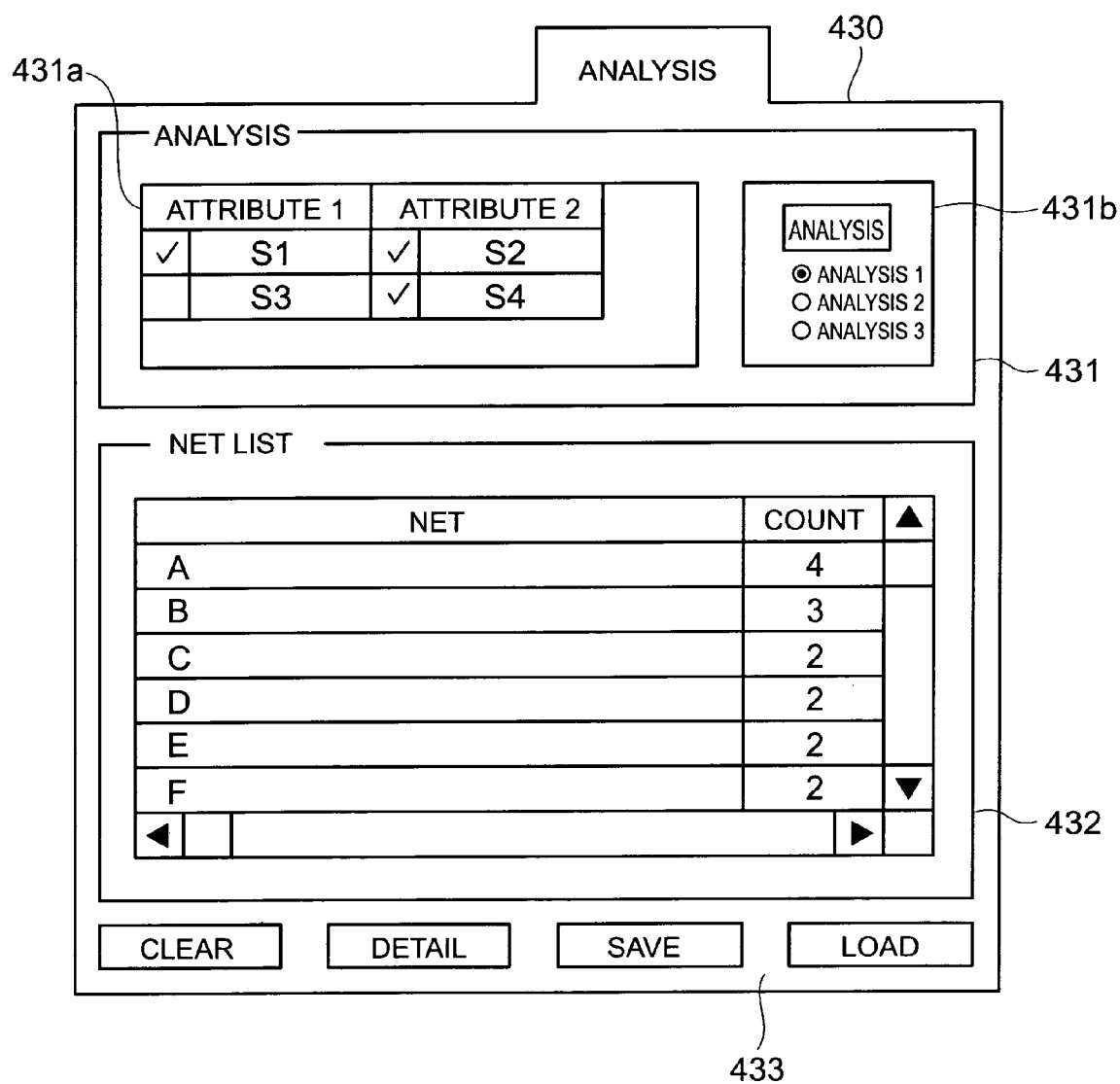
FIG. 13 is a configuration diagram showing another example of an operation screen displayed in an analysis operation region.

Subsequently, a configuration example of the analysis operation region 403 provided on the right side of the screen of the analysis window 400 will be described. In the present example, the operation screen displayed in the analysis operation region 403 can be switched among three screens, position adjustment operation screen 410, region setting operation screen 420, and analysis operation screen 430 shown in FIGS. 11 to 13, respectively. Among these operation screens, the position adjustment operation screen 410 of FIG. 11 is used in control of the processing executed in the position adjuster 133 of the failure analyzer 13 (cf. FIG. 2). The region setting operation screen 420 of FIG. 12 is used in control of the processing executed in the region setter 131. The analysis operation screen 430 of FIG. 13 is used in control of the processing executed in the net information analyzer 132 and in the display of the analysis result obtained.

First, the position adjustment operation screen 410 shown in FIG. 11 will be described. In this configuration example, a specific method of position alignment between the observed image P1, P2 and the layout image P3 by the position adjuster 133 is a method of designating three appropriate points in the pattern image P1, designating three corresponding points in the layout image P3, and effecting position adjustment from coordinates of those points. This method may also be modified to designate four or more points and perform the position alignment based thereon according to need.

In corresponding thereto, the operation screen 410 is provided with a position adjustment data setting region 411 for setting three points to be used in the position alignment for each of the pattern image P1 and the layout image P3. This setting of three points can be implemented, for example, by a method of setting the points through manipulation of a mouse on an image displayed in the image display region 401 in the analysis window 400, or by a method of entering coordinates of points to be set, as numerical data. The position adjustment of the images with three points is performed, for example, by θ correction to calculate an inclination between the pattern image P1 and the layout image P3 from the positions of the three points set, and to incline the pattern image P1 and the failure observed image P2, based thereon. For the θ correction, it is preferable to incline the pattern image P1 relative to the layout image P3, because the layout image P3 is true values of design data. However, it is also possible to incline the layout image P3 relative to the pattern image P1 according to the obtained inclination.

The operation screen 410 of FIG. 11 is further provided with an image adjustment region 412. This image adjustment region 412 permits the operator to manually carry out fine adjustment of position alignment, by carrying out such operation as rotation of the pattern image P1 (θ correction), movement of the layout image P3 (fine adjustment of position), or zooming of the layout image (enlargement/reduction). A button display region 413 displaying necessary operation buttons is provided below the regions 411, 412.

Next, the region setting operation screen 420 shown in FIG. 12 will be described. This operation screen 420 is provided with an analysis region setting region 421 for giving instructions necessary for setting of a plurality of analysis regions by the region setter 131, and an analysis region display region 422 for displaying information of each analysis region thus set. FIG. 12 shows display of coordinate data corresponding to four analysis regions of analysis regions 1 to 4 in the display region 422.

In this configuration example, two types of attributes, attribute 1 and attribute 2, can be set for each of the analysis regions 1 to 4. FIG. 12 shows an example wherein attribute "S1" is set as attribute 1 for the analysis region 1, attribute "S2" as attribute 2 for the analysis region 2, attribute "S3" as attribute 1 for the analysis region 3, and attribute "S4" as attribute 2 for the analysis region 4. A button display region 423 displaying necessary operation buttons is provided below the regions 421, 422.

Each of the above-described attributes is stored as linked with positional information of the analysis region (e.g., left upper and right lower coordinates of a rectangular analysis region). These pieces of information can be saved and read into and from a file or the like. For example, in a case where the analysis is carried out for the same positions of different devices, the information of the saved file is loaded, which eliminates a need for again drawing the regions and again setting their attributes, and which is useful in identifying which attribute (e.g., nondefective emission or the like) is owned by a reaction part thereof.

Next, the analysis operation screen 430 shown in FIG. 13 will be described. This operation screen 430 is provided with a failure analysis instruction region 431 for giving instructions necessary for execution of the failure analysis by the net information analyzer 132, and an analysis result display region 432 for displaying the analysis result obtained. In FIG. 13 the display region 432 presents the display of a list of names of nets obtained as an analysis result, and counts of passages of the nets through the analysis regions (net list). A button display region 433 displaying necessary operation buttons is provided below the regions 431, 432.

The failure analysis instruction region 431 is provided with a first instruction region 431a for selection of whether each analysis region is to be used in the failure analysis, for the attributes set for the respective analysis regions, and a second instruction region 431b for giving instructions for a specific condition of analysis (analysis 1-analysis 3) and for execution of the analysis. A method of selecting the analysis regions in this case can be a selection method of performing the failure analysis, using the analysis regions with checked attributes in the first instruction region 431a (attributes S1, S2, and S4 in the example of FIG. 11) and the analysis regions without any attribute set and not using the analysis region with the attribute not checked in the first instruction region 431a (attribute S3 in the example of FIG. 11), for example, in the failure analysis by the net information analyzer 132.

The configuration as described above is useful to various cases, for example, a case where, for each of parts that constantly emit light regardless of the presence/absence of a failure (e.g., parts of nondefective emissions), an analysis region with an attribute indicating it is set and the analysis region is eliminated from objects of the failure analysis. This can improve the efficiency of the analysis of failure of the semiconductor device.

Furthermore, the second instruction region 431b for instructions for the analysis condition is preferably configured in a configuration where a specific condition for extraction of nets can be set; for example, where the failure observed image is an emission image, only nets having wiring ends in the analysis region are extracted; where the failure observed image is an OBIRCH image, nets passing the interior of the analysis region are also extracted in addition to the nets having wiring ends in the analysis region. Such condition setting may also be arranged to be automatically selected according to the type of the failure observed image or the like.

Specifically, nets constituting a semiconductor device are routed so as to connect circuits such as transistors, and there are end points of the nets connected to the transistors. Emission of light is mainly weak emission due to switching of the transistors, and abnormal emission of light is induced mainly by a leak current of the transistors. The emission due to switching also occurs in nondefectives, and it can be discriminated by adding an attribute to the analysis region. In such an emission image, a net with an end point existing in a reaction region of the emission image is often associated with a circuit to cause emission of light, and a net passing the reaction region is not associated with the circuit to cause emission of light. Therefore, in the case of the failure analysis using the emission image, it is preferable to extract only the nets having the wiring end in the analysis region as described above.

On the other hand, the OBIRCH image is focused mainly on detection of a failure in the nets and also permits detection of a failure in transistor parts or the like. In the failure analysis using the OBIRCH image, it is thus preferable to also extract the nets passing the interior of the analysis region in addition to the nets having the wiring end in the analysis region as described above.

Figure 14:
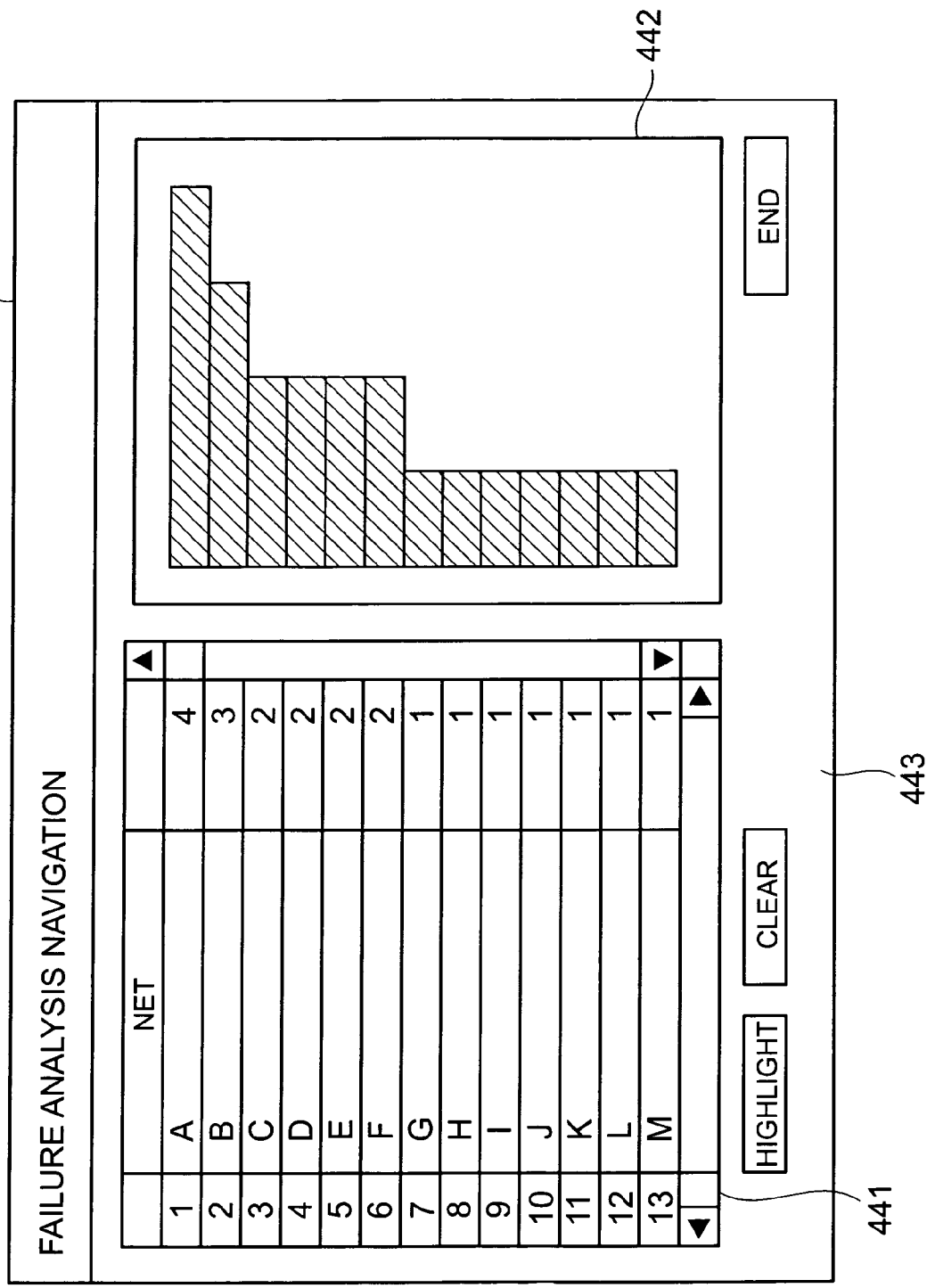
FIG. 14 is a configuration diagram showing an example of a display window displayed in a display device.

In the present configuration example, a net list display window 440 shown in FIG. 14 can also be displayed by a "detail" button in the button display region 433. This display window 440 has a net list display region 441 located on the left side of the screen, and a graph display region 442 displaying a graph (histogram) of the net list, located on the right side of the screen. The use of this display window 440 facilitates the operator's grasping the result of the failure analysis obtained.

The display window 440 of FIG. 14 enables highlight display of a selected net on the layout image by a "highlight" button in a button display region 443 in the lower part. In a case where the additional analysis information is acquired by the additional analysis information acquirer 134 as described above with FIG. 2, the nets determined to be defective by the analysis information may be colored in the net list display region 441 or in the graph display region 442. Where a net on the layout image is selected through such input means as a keyboard or a mouse, an analysis region where the net passes may be displayed with a different color to notify the operator of it.

The semiconductor failure analysis apparatus, failure analysis method, failure analysis program, and failure analysis system according to the present invention are not limited to the above-described embodiment and configuration examples, but can be modified in various ways. For example, the analysis window 400 was exemplified in FIG. 10, as an analysis screen for displaying the superimposed image generated by the superimposed image generator 141, in the display device 40, but it is also possible to use analysis screens of various configurations, without having to be limited to the exemplified configuration.

The present invention is applicable as the semiconductor failure analysis apparatus, failure analysis method, failure analysis program, and failure analysis system capable of securely and efficiently carrying out the analysis of the failure of the semiconductor device with the use of the observed image.

The semiconductor failure analysis apparatus according to the above embodiment is a semiconductor failure analysis apparatus for analyzing a failure of a semiconductor device, using an observed image thereof, comprising: (1) inspection information acquiring means for acquiring inspection information containing at least a pattern image being a normal observed image of the semiconductor device, as the observed image; (2) layout information acquiring means for acquiring layout information containing a layout image of the semiconductor device; (3) failure analyzing means for analyzing a failure of the semiconductor device with reference to the observed image; and (4) information display controlling means for letting display means display information about an analysis of the failure of the semiconductor device, (5) wherein the information display controlling means has superimposed image generating means for generating a superimposed image in which the pattern image and the layout image are superimposed, as an image of the semiconductor device to be displayed by the display means, and transmittance setting means for setting a transmittance of the layout image relative to the pattern image in the superimposed image.

The semiconductor failure analysis method is a semiconductor failure analysis method of analyzing a failure of a semiconductor device, using an observed image thereof, comprising: (a) an inspection information acquiring step of acquiring inspection information containing at least a pattern image being a normal observed image of the semiconductor device, as the observed image; (b) a layout information acquiring step of acquiring layout information containing a layout image of the semiconductor device; (c) a failure analyzing step of analyzing a failure of the semiconductor device with reference to the observed image; (d) an information displaying step of letting display means display information about an analysis of the failure of the semiconductor device; (e) a superimposed image generating step of generating a superimposed image in which the pattern image and the layout image are superimposed, as an image of the semiconductor device to be displayed by the display means; and (f) a transmittance setting step of setting a transmittance of the layout image relative to the pattern image in the superimposed image.

The semiconductor failure analysis program is a program for letting a computer execute a semiconductor failure analysis for analyzing a failure of a semiconductor device, using an observed image thereof, the program letting the computer execute: (a) an inspection information acquiring process for acquiring inspection information containing at least a pattern image being a normal observed image of the semiconductor device, as the observed image; (b) a layout information acquiring process of acquiring layout information containing a layout image of the semiconductor device; (c) a failure analyzing process of analyzing a failure of the semiconductor device with reference to the observed image; (d) an information displaying process of letting display means display information about an analysis of the failure of the semiconductor device; (e) a superimposed image generating process of generating a superimposed image in which the pattern image and the layout image are superimposed, as an image of the semiconductor device to be displayed by the display means; and (f) a transmittance setting process of setting a transmittance of the layout image relative to the pattern image in the superimposed image.

The semiconductor failure analysis system has the configuration comprising: the semiconductor failure analysis apparatus described above; inspection information supplying means for supplying the inspection information to the semiconductor failure analysis apparatus; layout information supplying means for supplying the layout information to the semiconductor failure analysis apparatus; and the display means for displaying the information about the analysis of the failure of the semiconductor device.

Here the failure analysis apparatus is preferably configured as follows: the inspection information acquiring means further acquires as the observed image, a failure observed image containing reaction information arising from a failure, which is obtained by conducting an inspection of the failure, the superimposed image generating means generates the superimposed image in which the failure observed image is further superimposed on the pattern image and the layout image, and the information display controlling means has second transmittance setting means for setting a transmittance of the failure observed image relative to the pattern image and the layout image in the superimposed image, in addition to the transmittance setting means.

Similarly, the failure analysis method is preferably configured as follows: the inspection information acquiring step comprises further acquiring as the observed image a failure observed image containing reaction information arising from a failure, obtained by conducting an inspection of the failure, the superimposed image generating step comprises generating the superimposed image in which the failure observed image is further superimposed on the pattern image and the layout image, and the failure analysis method comprises a second transmittance setting step of setting a transmittance of the failure observed image relative to the pattern image and the layout image in the superimposed image, in addition to the transmittance setting step.

Similarly, the failure analysis program is preferably configured as follows: the inspection information acquiring process comprises further acquiring as the observed image a failure observed image containing reaction information arising from a failure, obtained by conducting an inspection of the failure, the superimposed image generating process comprises generating the superimposed image in which the failure observed image is further superimposed on the pattern image and the layout image, and the program lets the computer execute a second transmittance setting process of setting a transmittance of the failure observed image relative to the pattern image and the layout image in the superimposed image, in addition to the transmittance setting process.

When the failure observed image is further superimposed in addition to the pattern image and the layout image and the transmittance thereof is made variable as described above, it becomes feasible to readily identify each of the pattern image, the layout image, the failure observed image, and superposition thereof through appropriate setting of the transmittance. Therefore, the efficiency of the analysis of the failure of the semiconductor device with the use of the observed image can be further improved.

The failure analysis apparatus is preferably configured so that the failure analyzing means has position adjusting means for performing position adjustment between the observed image containing at least the pattern image, and the layout image with reference to the pattern image and the layout image. Similarly, the failure analysis method is preferably configured to comprise a position adjusting step of performing position adjustment between the observed image containing at least the pattern image, and the layout image with reference to the pattern image and the layout image. Similarly, the failure analysis program is preferably configured to let the computer execute a position adjusting process of performing position adjustment between the observed image containing at least the pattern image, and the layout image with reference to the pattern image and the layout image. Where the failure observed image is acquired as another observed image in addition to the pattern image, the foregoing position adjustment is preferably arranged to effect position alignment between the observed images including the pattern image and the failure observed image, and the layout image with reference to the pattern image and the layout image.

When the position adjustment with the layout image is effected with the use of the pattern image as described above, the accuracy of the analysis of the failure of the semiconductor device can be improved. Particularly, where the failure observed image is acquired as another observed image in addition to the pattern image, the aforementioned position alignment is effective because the pattern image is acquired in a state in which it is aligned in position with the failure observed image.

As a specific display configuration of the superimposed image in the display means, the failure analysis apparatus can adopt a configuration wherein the information display controlling means has analysis screen generating means for generating an analysis screen having an image display region for displaying the superimposed image generated by the superimposed image generating means, and an analysis operation region to be used in an operation concerning the analysis of the failure conducted by the failure analyzing means, as a screen to be displayed by the display means. Similarly, the failure analysis method can adopt a method comprising an analysis screen generating step of generating an analysis screen having an image display region for displaying the superimposed image generated in the superimposed image generating step, and an analysis operation region to be used in an operation concerning the analysis of the failure conducted in the failure analyzing step, as a screen to be displayed by the display means. Similarly, the failure analysis program can adopt a configuration for letting the computer execute an analysis screen generating process of generating an analysis screen having an image display region for displaying the superimposed image generated in the superimposed image generating process, and an analysis operation region to be used in an operation concerning the analysis of the failure conducted in the failure analyzing process, as a screen to be displayed by the display means.

The failure analysis apparatus may be configured to comprise layout image display controlling means for letting the display means display the layout image, separately from the display of the superimposed image by the information display controlling means. Similarly, the failure analysis method may be configured to comprise a layout image displaying step for letting the display means display the layout image, separately from the display of the superimposed image. Similarly, the failure analysis program may be configured to let the computer execute a layout image displaying process of letting the display means display the layout image, separately from the display of the superimposed image.

What is claimed is:

1. A semiconductor failure analysis apparatus for analyzing a failure of a semiconductor device, using an observed image thereof, comprising:

inspection information acquiring means for acquiring inspection information containing at least a pattern image being a normal observed image of the semiconductor device obtained by image acquiring means in a semiconductor inspection apparatus, and a failure observed image containing reaction information arising from a failure obtained by conducting an inspection of the failure by the semiconductor inspection apparatus, as the observed image;

layout information acquiring means for acquiring layout information containing a layout image generated from design information of the semiconductor device;

failure analyzing means for analyzing a failure of the semiconductor device with reference to the observed image; and information display controlling means for letting display means display information about an analysis of the failure of the semiconductor device, wherein the information display controlling means has superimposed image generating means for generating a superimposed image in which the layout image is superimposed on the pattern image, and the failure observed image is further superimposed on the pattern image and the layout image, as an image of the semiconductor device to be displayed by the display means, first transmittance setting means for variably setting a first transmittance of the layout image relative to the pattern image, corresponding to a superimposing ratio between the layout image and the pattern image, in the superimposed image, and second transmittance setting means for variably setting a second transmittance of the failure observed image relative to the pattern image and the layout image, corresponding to a superimposing ratio of the failure observed image, in the superimposed image, wherein the superimposed image generating means generates the superimposed image by superimposing the layout image on the pattern image and further superimposing the failure observed image on the pattern image and the layout image by using the superimposing ratios determined from the first transmittance and the second transmittance variably set by the first transmittance setting means and the second transmittance setting means, and wherein the information display controlling means has analysis screen generating means for generating an analysis screen having an image display region for displaying the superimposed image generated by the superimposed image generating means, and a display adjustment region provided with a first transmittance setting part used for setting of the first transmittance in the first transmittance setting means and a second transmittance setting part used for setting of the second transmittance in the second transmittance setting means, as a screen to be displayed by the display means.

2. The failure analysis apparatus according to claim 1, wherein the failure analyzing means has position adjusting means for performing position adjustment between the observed image including at least the pattern image and the failure observed image, and the layout image with reference to the pattern image and the layout image.

3. The failure analysis apparatus according to claim 1, wherein analysis screen generating means generates the analysis screen having an analysis operation region to be used in an operation concerning the analysis of the failure conducted by the failure analyzing means, in addition to the image display region and the display adjustment region as a screen to be displayed by the display means.

4. The failure analysis apparatus according to claim 1, comprising layout image display controlling means for letting the display means display the layout image, separately from the display of the superimposed image by the information display controlling means.

5. The failure analysis apparatus according to claim 1, wherein the display adjustment region in the analysis screen is provided with a pattern image display switch part for switching the display of the pattern image on or off, a layout image display switch part for switching the display of the layout image on or off, and a failure observed image display switch part for switching the display of the failure observed image on or off, in addition to the first transmittance setting part and the second transmittance setting part.

6. The failure analysis apparatus according to claim 1, wherein the failure observed image acquired by the inspection information acquiring means is an emission image or an OBIRCH image.

7. A semiconductor failure analysis method of analyzing a failure of a semiconductor device by using a computer, using an observed image thereof, comprising:

an inspection information acquiring step of acquiring inspection information containing at least a pattern image being a normal observed image of the semiconductor device obtained by acquiring an image with a semiconductor inspection apparatus, and a failure observed image containing reaction information arising from a failure obtained by conducting an inspection of the failure by the semiconductor inspection apparatus, as the observed image;

a layout information acquiring step of acquiring layout information containing a layout image generated from design information of the semiconductor device;

a failure analyzing step of analyzing a failure of the semiconductor device by using the computer with reference to the observed image;

an information displaying step of letting display means, which is connected to the computer, display information about an analysis of the failure of the semiconductor device;

a superimposed image generating step of generating a superimposed image by using the computer in which the layout image is superimposed on the pattern image, and the failure observed image is further superimposed on the pattern image and the layout image, as an image of the semiconductor device to be displayed by the display means;

a first transmittance setting step of variably setting a first transmittance of the layout image relative to the pattern image, corresponding to a superimposing ratio between the layout image and the pattern image, in the superimposed image; and a second transmittance setting step of variably setting a second transmittance of the failure observed image relative to the pattern image and the layout image, corresponding to a superimposing ratio of the failure observed image, in the superimposed image, and wherein the superimposed image generating step generates the superimposed image by superimposing the layout image on the pattern image and further superimposing the failure observed image on the pattern image and the layout image by using the superimposing ratios determined from the first transmittance and the second transmittance variably set by the first transmittance setting step and the second transmittance setting step, and the method further comprising an analysis screen generating step of generating an analysis screen by using the computer having an image display region for displaying the superimposed image generated in the superimposed image generating step, and a display adjustment region provided with a first transmittance setting part used for setting of the first transmittance in the first transmittance setting step and a second transmittance setting part used for setting of the second transmittance in the second transmittance setting step, as a screen to be displayed by the display means.

8. The failure analysis method according to claim 7, comprising a position adjusting step of performing position adjustment by using the computer between the observed image including at least the pattern image and the failure observed image, and the layout image with reference to the pattern image and the layout image.

9. The failure analysis method according to claim 7, wherein the analysis screen generating step comprises generating the analysis screen having an analysis operation region to be used in an operation concerning the analysis of the failure conducted in the failure analyzing step, in addition to the image display region and the display adjustment region.

10. The failure analysis method according to claim 6, comprising a layout image displaying step for letting the display means display the layout image, separately from the display of the superimposed image.

11. The failure analysis method according to claim 7, wherein the display adjustment region in the analysis screen is provided with a pattern image display switch part for switching the display of the pattern image on or off, a layout image display switch part for switching the display of the layout image on or off, and a failure observed image display switch part for switching the display of the failure observed image on or off, in addition to the first transmittance setting part and the second transmittance setting part.

12. The failure analysis method according to claim 7, wherein the failure observed image acquired by the inspection information acquiring step is an emission image or an OBIRCH image.

13. A program stored on a computer readable medium for letting a computer execute a semiconductor failure analysis for analyzing a failure of a semiconductor device, using an observed image thereof, the semiconductor failure analysis program letting the computer execute:

an inspection information acquiring process for acquiring inspection information containing at least a pattern image being a normal observed image of the semiconductor device obtained by acquiring an image with a semiconductor inspection apparatus, and a failure observed image containing reaction information arising from a failure obtained by conducting an inspection of the failure by the semiconductor inspection apparatus, as the observed image;

a layout information acquiring process of acquiring layout information containing a layout image generated from design information of the semiconductor device;

a failure analyzing process of analyzing a failure of the semiconductor device with reference to the observed image;

an information displaying process of letting display means display information about an analysis of the failure of the semiconductor device;

a superimposed image generating process of generating a superimposed image in which the layout image is superimposed on the pattern image, and the failure observed image is further superimposed on the pattern image and the layout image, as an image of the semiconductor device to be displayed by the display means;

a first transmittance setting process of variably setting a first transmittance of the layout image relative to the pattern image, corresponding to a superimposing ratio between the layout image and the pattern image, in the superimposed image; and a second transmittance setting process of variably setting a second transmittance of the failure observed image relative to the pattern image and the layout image, corresponding to a superimposing ratio of the failure observed image, in the superimposed image, and wherein the superimposed image generating process generates the superimposed image by superimposing the layout image on the pattern image and further superimposing the failure observed image on the pattern image and the layout image by using the superimposing ratios determined from the first transmittance and the second transmittance variably set by the first transmittance setting process and the second transmittance setting process, and the program letting the computer execute an analysis screen generating process of generating an analysis screen having an image display region for displaying the superimposed image generated in the superimposed image generating process, and a display adjustment region provided with a first transmittance setting part used for setting of the first transmittance in the first transmittance setting process and a second transmittance setting part used for setting of the second transmittance in the second transmittance setting process, as a screen to be displayed by the display means.

14. The failure analysis program according to claim 13, the program letting the computer execute a position adjusting process of performing position adjustment between the observed image including at least the pattern image and the failure observed image, and the layout image with reference to the pattern image and the layout image.

15. The failure analysis program according to claim 11, wherein the analysis screen generating process comprises generating analysis screen having an analysis operation region to be used in an operation concerning the analysis of the failure conducted in the failure analyzing process, in addition to the image display region and the display adjustment region.

16. The failure analysis program according to claim 11, the program letting the computer execute a layout image displaying process of letting the display means display the layout image, separately from the display of the superimposed image.

17. A semiconductor failure analysis system comprising:
the semiconductor failure analysis apparatus as defined in claim 1;
inspection information supplying means for supplying the inspection information to the semiconductor failure analysis apparatus;
layout information supplying means for supplying the layout information to the semiconductor failure analysis apparatus; and
the display means for displaying information about the analysis of the failure of the semiconductor device.

18. The failure analysis program according to claim 13, wherein the display adjustment region in the analysis screen is provided with a pattern image display switch part for switching the display of the pattern image on or off, a layout image display switch part for switching the display of the layout image on or off, and a failure observed image display switch part for switching the display of the failure observed image on or off, in addition to the first transmittance setting part and the second transmittance setting part.

19. The failure analysis program according to claim 13, wherein the failure observed image acquired by the inspection information acquiring process is an emission image or an OBIRCH image.

* * * * *